US007020618B1

(12) United States Patent
Ward

(10) Patent No.: US 7,020,618 B1
(45) Date of Patent: Mar. 28, 2006

(54) METHOD AND SYSTEM FOR CUSTOMER SERVICE PROCESS MANAGEMENT

(76) Inventor: Richard E. Ward, 1950 Gough St. #102, San Francisco, CA (US) 94109

( * ) Notice: Subject to any disclaimer, the term of this patent is extended or adjusted under 35 U.S.C. 154(b) by 0 days.

(21) Appl. No.: 09/427,149

(22) Filed: Oct. 25, 1999

(51) Int. Cl.
*G06Q 10/00* (2006.01)

(52) U.S. Cl. .............................. 705/8; 705/7

(58) Field of Classification Search ............... 705/2, 705/3, 7, 8, 1
See application file for complete search history.

(56) References Cited

U.S. PATENT DOCUMENTS

| | | | |
|---|---|---|---|
| 5,692,220 A * | 11/1997 | Diamond et al. ........... | 600/368 |
| 5,706,452 A | 1/1998 | Ivanov | |
| 5,721,912 A | 2/1998 | Stepczyk et al. | |
| 5,721,913 A | 2/1998 | Ackroff et al. | |
| 5,721,943 A | 2/1998 | Johnson | |
| 5,734,837 A | 3/1998 | Flores et al. | |
| 5,745,687 A | 4/1998 | Randell | |
| 5,754,857 A | 5/1998 | Gadol | |
| 5,754,901 A | 5/1998 | Stoneham et al. .......... | 396/319 |
| 5,768,506 A | 6/1998 | Randell | |
| 5,772,585 A * | 6/1998 | Lavin et al. ................ | 128/920 |
| 5,774,661 A | 6/1998 | Chatterjee et al. | |
| 5,794,208 A * | 8/1998 | Goltra ........................... | 705/1 |
| 5,799,297 A | 8/1998 | Goodridge et al. ............ | 707/1 |
| 5,819,022 A | 10/1998 | Bandat | |
| 5,823,948 A * | 10/1998 | Ross et al. .................. | 600/300 |
| 5,826,020 A | 10/1998 | Randell | |
| 5,826,237 A * | 10/1998 | Macrae et al. ................ | 705/2 |
| 5,826,239 A | 10/1998 | Du et al. ....................... | 705/8 |
| 5,845,255 A * | 12/1998 | Mayaud .......................... | 705/3 |

(Continued)

FOREIGN PATENT DOCUMENTS

WO    WO 97/32271    *    9/1997

(Continued)

OTHER PUBLICATIONS

Logician, medicalogic.com, May 8, 1998 [retreievd Aug. 14, 2003], pp. 1-96, retrieved from: Google.com and archive.org.*

(Continued)

*Primary Examiner*—Tariq R. Hafiz
*Assistant Examiner*—Beth Van Doren
(74) *Attorney, Agent, or Firm*—Pillsbury Winthrop Shaw Pittman LLP

(57) ABSTRACT

A method and system for managing customer service processes for individual customers and populations of customers. In a specific embodiment within the health care field, a clinician creates or updates a draft care plan for a patient using generic or locally-adapted template metadata and tailors the draft care plan to the particular patient. The draft care plan includes a list of specific services (health care interventions) to be provided to the patient. The draft care plan can be routed to members of an inter-disciplinary team for input. Once finalized, workflow processes are instantiated for each intervention on the care plan. An itinerary is created for any required patient encounters, optimized using an algorithm that considers pre-existing process instances. A workflow automation server manages the execution of each workflow process instance, invoking resources according to workflow process specification metadata and workflow task type metadata. Care plans and encounter itineraries are automatically translated to a patient-understandable form and made available to patients online and via printed copy. Clinical practice and outcomes data are analyzed to identify opportunities for improvement of the metadata. The method and system also allows for the selection of a population of patients, the analysis of population data to identify opportunities for interventions (needed services), and the initiation of population interventions through batch updates to individual care plans.

71 Claims, 12 Drawing Sheets

U.S. PATENT DOCUMENTS

| | | | |
|---|---|---|---|
| 5,848,393 A | 12/1998 | Goodridge et al. | 705/8 |
| 5,860,066 A | 1/1999 | Rouse | 705/1 |
| 5,867,824 A | 2/1999 | Saito et al. | 705/9 |
| 5,870,545 A | 2/1999 | Davis et al. | |
| 5,870,711 A | 2/1999 | Huffman | 705/8 |
| 5,878,398 A | 3/1999 | Tokuda et al. | 705/8 |
| 5,890,130 A | 3/1999 | Cox et al. | 705/7 |
| 5,890,133 A | 3/1999 | Ernst | 705/7 |
| 5,905,496 A | 5/1999 | Lau et al. | 345/339 |
| 5,918,226 A | 6/1999 | Tarumi et al. | 707/10 |
| 5,930,512 A | 7/1999 | Boden et al. | |
| 5,937,388 A | 8/1999 | Davis et al. | 705/8 |
| 5,940,804 A | 8/1999 | Turley et al. | 705/9 |
| 5,960,403 A * | 9/1999 | Brown | 705/2 |
| 5,974,389 A * | 10/1999 | Clark et al. | 705/3 |
| 6,037,940 A * | 3/2000 | Schroeder et al. | 345/763 |
| 6,047,259 A * | 4/2000 | Campbell et al. | 705/2 |
| 6,161,095 A * | 12/2000 | Brown | 705/2 |
| 6,304,848 B1 * | 10/2001 | Singer | 705/3 |
| 6,381,576 B1 * | 4/2002 | Gilbert | 705/2 |
| 6,434,531 B1 * | 8/2002 | Lancelot et al. | 705/3 |
| 6,587,830 B1 * | 7/2003 | Singer | 705/3 |
| 6,804,656 B1 * | 10/2004 | Rosenfeld et al. | 705/3 |

FOREIGN PATENT DOCUMENTS

WO    WO 98/50871    * 11/1998

OTHER PUBLICATIONS

Purkinje Inc., www.purkinje.com, May 25, 1998-Sep. 12, 1999 [retrieved Aug. 14, 2003], pp. 1-22, retrieved from: Google.com and archive.org.*

* cited by examiner

870 — How are you able to perform the following activities? (indicate single best answer for each activity):

| | 876 — No problem. | Can do it, but with a little difficulty. | Can do it, but with great difficulty. | Cannot do it. |
|---|---|---|---|---|
| 875 — Walk up one flight of stairs. | 878 — ☐ | ☐ | ☐ | ☐ |
| Walk for 5 minutes. | ☐ | ☐ | ☐ | ☐ |
| Walk for 15 minutes. | ☐ | ☐ | ☐ | ☐ |
| Carry grocery bags more than a few steps. | ☐ | ☐ | ☐ | ☐ |

METHOD AND SYSTEM FOR CUSTOMER SERVICE PROCESS MANAGEMENT

FIELD OF THE INVENTION

This invention relates to computer systems, and more particularly to workflow systems, and even more particularly to customer service process management systems or customer relationship management (CRM) systems.

DESCRIPTION OF THE RELATED ART

Service industries require planning and coordination of services across multiple service providers in multiple locations across time. This is particularly true in service industries offering complex professional services, including financial services, insurance, legal services, consulting services and health care services. In such industries, work can be conceptualized as falling into two categories. In the first category, service providers (or sales personnel serving as agents of service providers) work to develop a plan or proposal for services to be provided to a particular customer to meet their individual needs. In the second category, service providers work to deliver the services according to the plan or proposal. In recent years, computer-based systems have been developed to facilitate both of these categories of work.

In the first category, developing plans or proposals, computer-based systems have been developed in the context of services associated with products. "Product configurators" have been developed that allow entry of metadata describing product and service components and their logical relationships, then allow entry of information regarding a particular prospective customer, and then assist in the generation of complete, valid, non-ambiguous configurations, including needed services associated with products. For example, if a customer orders a particular computer system configuration, appropriate installation and training services are included in the configuration. Systems have been developed that query the user to determine the customer's needs and then generate a customized, printed proposal describing the features and benefits of products, including automobiles. In another example, a system uses rules to automatically generate a customized insurance policy document. In another example, a system generates project plans and specifications for proposed building construction projects. In the health care field, "template charting" systems have been developed to facilitate the preparation of medical chart notes, including the "plan of care" section, and medical order entry systems have been designed that offer pre-prepared "order sets" to facilitate quick, consistent entries and rule-driven "reminders" and "alerts" which alert the user about needed health care services or inappropriate services that have been proposed or ordered for the customer.

In the second category, service delivery, computer-based systems have been developed to manage the flow of work among a team of service providers. These systems are known as "groupware" or "workflow" or "workflow automation" systems. Workflow systems generally provide a capability for entering metadata describing the sequence of tasks or activities in a work process, the resources required to execute each task, and the data needed to manage the flow of activities and to execute each task. The component of a workflow system used to enter such metadata is variously known as a "workflow builder", a "workflow authoring tool" or a "process definition tool." Workflow systems also generally include a component that manages the execution of individual workflow instances, such as a workflow to process a particular insurance claim for a particular auto accident. This component is variously known as a "workflow engine," a "workflow automation server," or a "workflow enactment service." This component tracks the status of each workflow instance, determines what task is needed next, determines what human or system resources to marshal to execute the task, and communicates with those resources to transport the needed data to and from the resources. In these systems, an instance of a workflow is generally initiated by completing a computer-based form that provides the data needed to get the workflow started. Workflow systems increase the efficiency of service delivery, since they are able to route the right task to the right person or machine at the right time. They increase the consistency and quality of service delivery, since they track work according to metadata which can define best practices. They also increase the reliability of services, since bottlenecks and errors can be identified and managed. Some workflow systems provide a generic framework that can be adapted to a wide variety of service-delivery processes.

The emergence of the Internet has greatly increased the value of both categories of systems. For planning and proposal development work, the Internet facilitates access by field sales personnel or service providers and enables direct entry of customer data by customers. For example, web sites have been developed enabling prospective car buyers to enter preferences and receive a proposal for a car. For service delivery work, the Internet allows work to be distributed across organizational boundaries, geographic locations and disciplines.

Although these two types of systems have provided great benefits for consumers and service providers, there is an opportunity for significant improvement. First, the linkage or integration of the two categories of work (developing plans/proposals and service delivery) is poor. The form-based initiation for workflow instances in existing workflow systems works adequately for simple service-delivery processes, but is inadequate to use for planning of complex services where customers have multiple problems and needs that can only be met with a tailored collection of services. For example, in the health care field, existing medical order entry systems can handle the entry of a single laboratory, or even a set of orders commonly used for a particular purpose. But they are not up to the task of managing the creation of an overall plan of care for a patient with multiple health problems, particularly those that are being addressed by an inter-disciplinary team of health care service providers. And even for simple laboratory orders, existing order entry systems do not manage the entire process of communicating the results to the right people, escalating the communications process if people are unavailable, initiating follow-up services, etc.

Another inadequacy in service planning and proposal development systems is the difficulty in tailoring plans and proposals to the individual needs and problems of the customer, particularly given the large number of potential problems and the huge number of possible combinations of problems that a given customer may have. For example, in the health care domain, patients may have multiple health problems, selected from a universe of possible problems at least in the tens of thousands, and each of which may have a variety of different presentations. Managing metadata to handle this variation can be prohibitively expensive.

Another inadequacy is the difficulty in simultaneously meeting the needs of a large population of customers with changing and emerging needs. Frequent review of each individual customer's service plan is usually infeasible.

Many existing systems use rule-based alerts to identify erroneous or conflicting information, or reminders to identify missing needed services. But if there are a large number of such alerts and reminders, as are often required for complex professional services, maintaining the quality and accuracy of the associated metadata is difficult. As a result, the proportion of inappropriate alerts and reminders increases over time, creating a burden of users and eventually creating a "boy who cried wolf" problem where users ignore valid alerts and reminders because they have given up on them all.

In complex service industries, customers often have difficulty understanding service plans and service providers do not always have time to explain. Although some systems produce printed proposals with embedded explanatory material, this is not available in system that solves the other problems described herein.

In health care and some other service industries, it is a legal requirement that service providers formally document the services that they provide, as well as their plans for delivering services in the future. Documentation of services provided is also a requirement for fee-for-service billing. Creating service plans and documenting services provided for legal or billing purposes represents a duplication of work. Although there are systems designed to assist in the creation of medical chart notes, no existing system integrates this function into a flexible workflow automation system to eliminate this duplication.

Existing face-to-face processes for gathering input from multi-disciplinary teams of service providers into service plans is prohibitively expensive and logistically difficult for busy teams. For example, in the health care field, "tumor boards" and "inter-disciplinary clinics" are used to provide a mechanism for users in different disciplines and specialties to provide input and collaborate in the development of a plan of care for a patient. But the great expense of these meetings relegates this practice to only the most serious and academically interesting cases within advanced medical centers. Systems are not available to incorporate inter-disciplinary input into the development of a care plan that can be used for automatic initiation of workflows to manage execution of the plan.

SUMMARY OF THE INVENTION

In view of the above, it is an object of the present invention to provide an automated system and method for customer service process management, including the inter-disciplinary preparation of service plans or proposals for individual customers, the automated management of the execution of such plans, and the population-level identification of needs and specific services to meet those needs.

It is another object of the invention to facilitate the creation, maintenance and continual improvement of the metadata needed for such a system.

A further object of the invention is to provide a system and method for customer service process management that allows for the automated generation of customer-understandable service plans, workflow status, and result information, provided directly to customers on-line or by conventional media.

A still further object of the invention is to provide a system for distributing service plan metadata and associated workflow metadata to service providers, such that the distributed metadata can be either used in the distributed form, or updated for personalization needed by a particular service provider.

These and other objects and advantages are obtained by providing for methods and systems for customer service process management. In one embodiment the present invention, the system includes at least one client computer used by customers and at least one client computer used by service providers, which are each interconnected via a communications network to certain ones of a database service computer, a workflow automation server computer, a web application server computer, and external server computers. Using such a system, customer service processes are managed both for individual customers and populations of customers.

In a specific embodiment within the health care field, a generic metadata supplier provides generic care plan templates, generic workflow process specifications, and generic workflow task type metadata to a service provider.

Then, a user such as a clinician associated with the service provider adapts the generic metadata or creates new metadata according to preferred specifications to obtain local metadata, including local care plan templates, local care process specifications and local workflow task type metadata. Then, a clinician or other user associated with the service provider creates or updates a draft care plan for a patient using the generic or local care plan template metadata and patient specific information. The draft care plan includes a list of specific services (i.e. health care interventions) to be provided to the patient. The draft care plan can be routed to members of an inter-disciplinary team for input.

Once the care plan is finalized, workflow processes are instantiated for each intervention in the care plan. An itinerary is created for any required patient encounter, optimized to account for pre-existing process instances. A workflow automation server manages the execution of each intervention, invoking resources according to the workflow process specification metadata and workflow task type metadata.

In another aspect, the present invention allows for the analysis of outcomes data to identify opportunities for improvement of the associated metadata. Graphical tools for managing metadata and automatic generation of feedback data regarding the appropriateness of metadata for reminders and alerts provides these capabilities.

The methods and systems according to the present invention also allow for the selection of a population of service customers, the analysis of population data to identify opportunities for needed services, and the initiation of specific services for the entire population through batch updates to individual service plans. The resulting updated service plans are then executed using the same method and system components described above.

BRIEF DESCRIPTION OF DRAWINGS

The above and other objects, features, and advantages of the present invention are further described in the detailed description which follows, with reference to the drawings by way of non-limiting exemplary embodiments of the present invention, wherein like reference numerals represent similar parts of the present invention throughout several views and wherein:

FIG. 6 is a diagram representing an example question data item.

DETAILED DESCRIPTION OF THE PRESENTLY PREFERRED EMBODIMENTS

The figures depict a preferred embodiment of the present invention for purposes of illustration only. One skilled in the art will readily recognize from the following discussion that alternative embodiments of the structures and methods illustrated herein may be employed without departing from the principles of the invention described herein.

Figure 1:
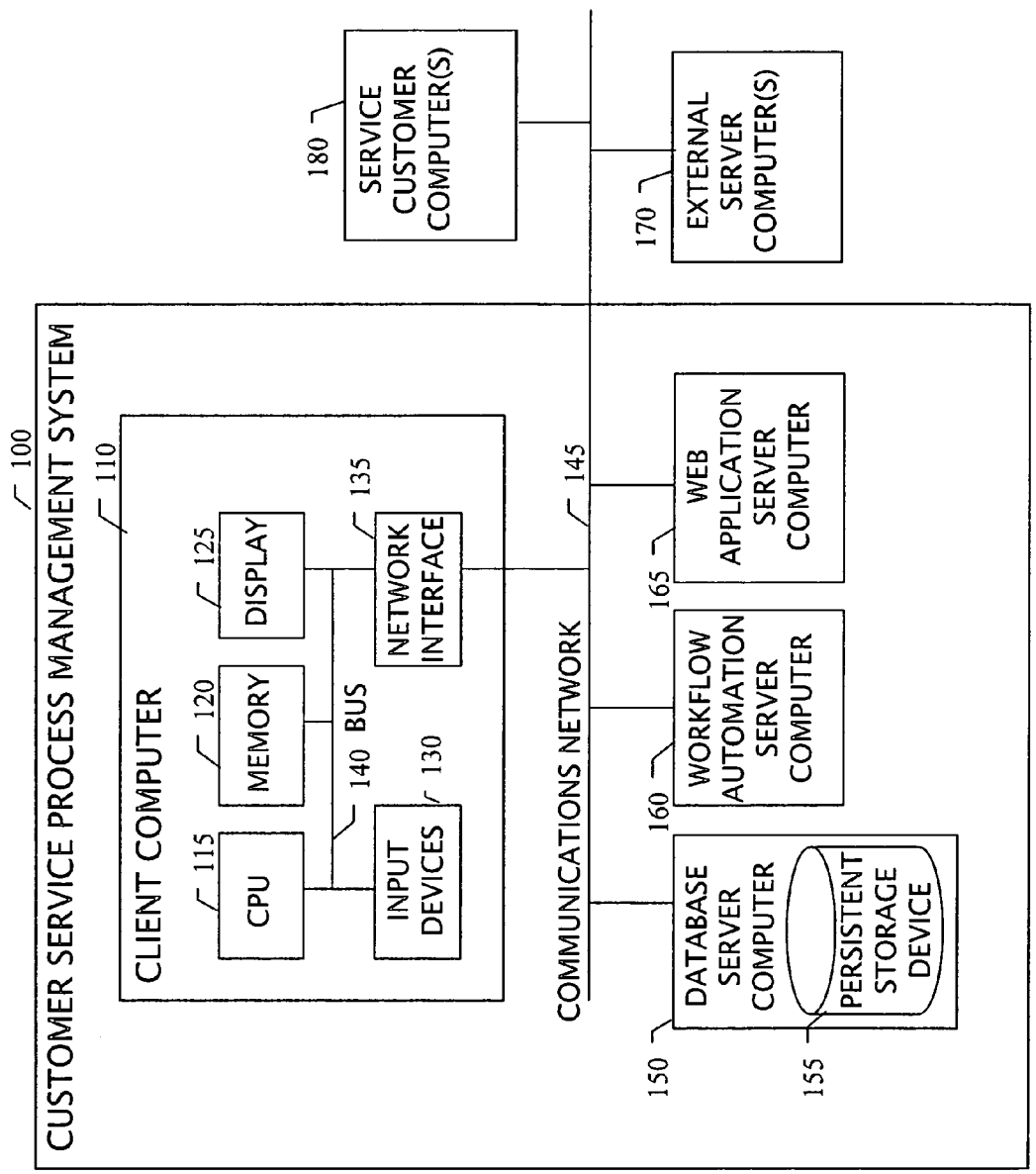
FIG. 1 is a block diagram of a computer-based system for customer service process management.

Referring to FIG. 1, there is shown a system 100 for managing customer service processes in accordance with the present invention. The major components of system 100 include at least one client computer 110, such as a based personal computer, containing a central processing unit (CPU) 115, memory 120, at least one display device 125, at least one input device 130 (such as a keyboard and a mouse pointing device), and a network interface 135. These components of the client computer 110 are interconnected via a bus 140. Customer service providers and customers directly interact with client computers such as the one illustrated as 110. The network interface 135 provides a means for communication between the client computer 110 and other computers on a communications network 145. The system 100 also includes a database server computer 150 for storing service customer data and metadata, a workflow automation server computer 160, and a web application server computer 165. Application programs, each containing program instructions correlated to the necessary functions being performed, are stored in corresponding memories for these computers and servers, to perform in the manner detailed below. Each of these computers is of conventional design, with internal components as generally described for the client computer 110. The database server computer 150 includes a persistent storage device 155, such as a hard disk drive. These computers may also be interconnected via communications network 145 to one or more external server computers 170, such as computers used for legacy systems within the various organizations involved in the customer service process. It should be noted that, although FIG. 1 illustrates the use of a single, separate computer serving as each of the client computer 110, database server computer 150, workflow automation server computer 160, web application server computer 165 and external server computer 170, many other embodiments are possible. In accordance with conventional network computing methods, several of these computer functions could be run on a single physical computer device. Alternatively, several of these computer functions could be distributed to be run on a plurality of physical computer devices. Also shown is a service customer computer 180, which can remotely contact the single separate computer, preferably via the Internet, to provide and receive information as discussed hereinafter.

Figure 2:
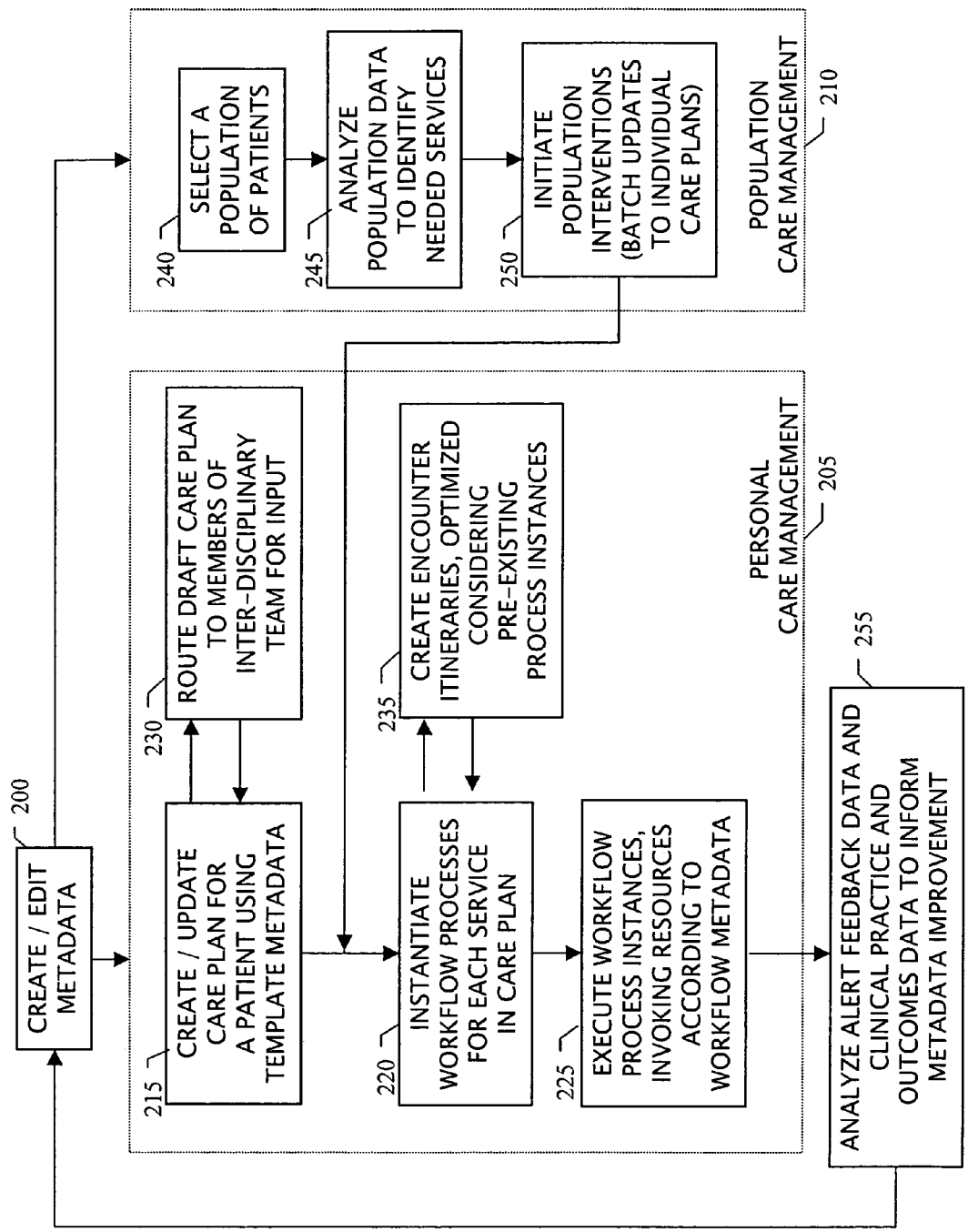
FIG. 2 is an overall process flow diagram of a process for using the system for personal care management, population care management, and metadata improvement.

Referring now to FIG. 2, the overall method for customer service process management is illustrated in an embodiment in the domain of health care delivery. It is understood that while the embodiment in the domain of health care delivery has certain novel and unique aspects, that the present invention also has unique aspects that are not limited to the domain of health care delivery. Accordingly, subsequent figures provide additional detail for the various parts of this overall method, and are described with reference to the domain of health care delivery. The first step 200 in this method is to create and edit the various types of metadata used by the system. These metadata, including libraries of generic metadata, which include structured sentence data items, and generic care plan templates and generic workflow process specification metadata, which include process specifications and report specifications are described in detail below, all of which are preferably obtained from a generic metadata supplier, which supplier preferably provides generic care plan template metadata as well as generic workflow specification metatadata and workflow task type metadata associated therewith. This generic metadata is preferably disseminated by the generic metadata supplier in generic metadata modules transmitted via the Internet to the service provider While described above as "generic metadata," it should be understood that the metadata will typically be highly specific to the type of plan that is being implemented. In many instances the service provider will use the generic plan metadata "as is," without modification. Since, however, this metadata is capable of being adapted to the needs of a particular service provider, the descriptor "generic" is used. Nevertheless, one of the important aspects of the present invention is the ability of the generic metadata supplier to provide information that is extremely current, and therefore can widely disseminate the most current medical treatments for a specific medical problem.

A user such as a clinician associated with the service provider organization can edit the received generic metadata or create new plan metadata according to preferred specifications to obtain local metadata. Of course, it is understood that the local metadata can be created in other manners as well.

Using generic or local plan metadata, including care plan template metadata, the user, typically the clinician, creates 215 a draft care plan for an individual patient or updates a pre-existing care plan for such a patient. This care plan is then stored in the database server computer 150.

Figure 3:
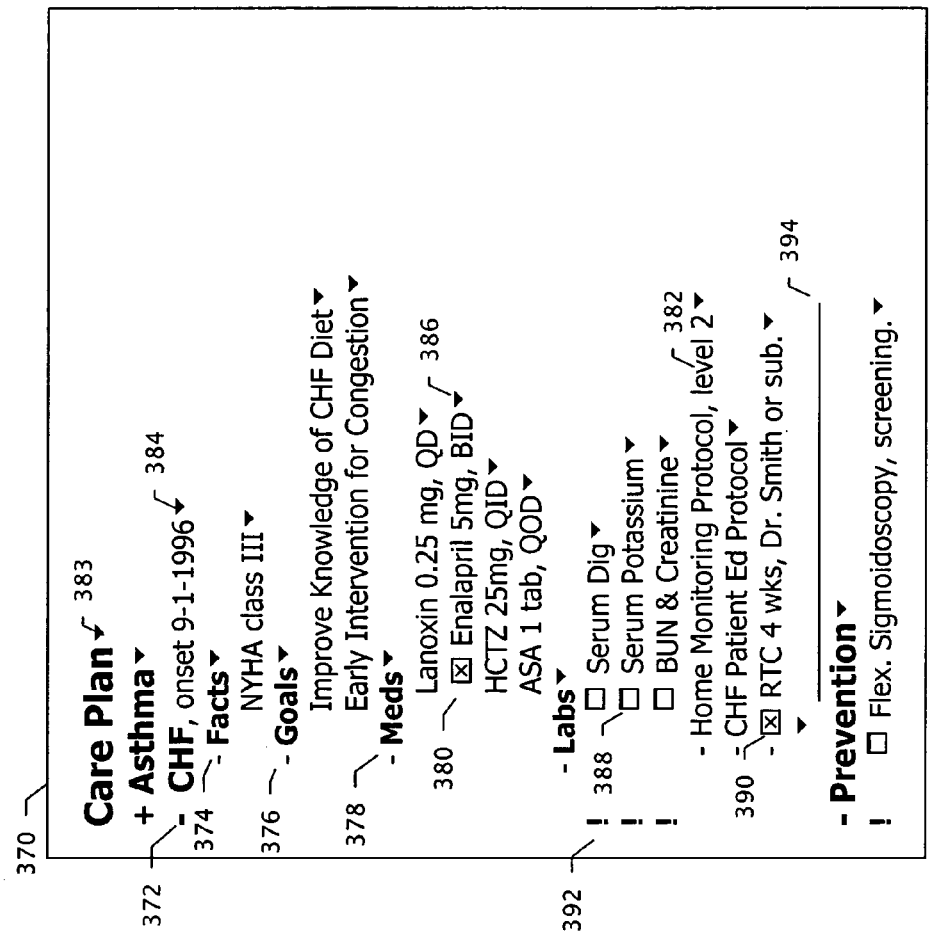
FIG. 3 is a diagram representing an example care plan
Figure 5:
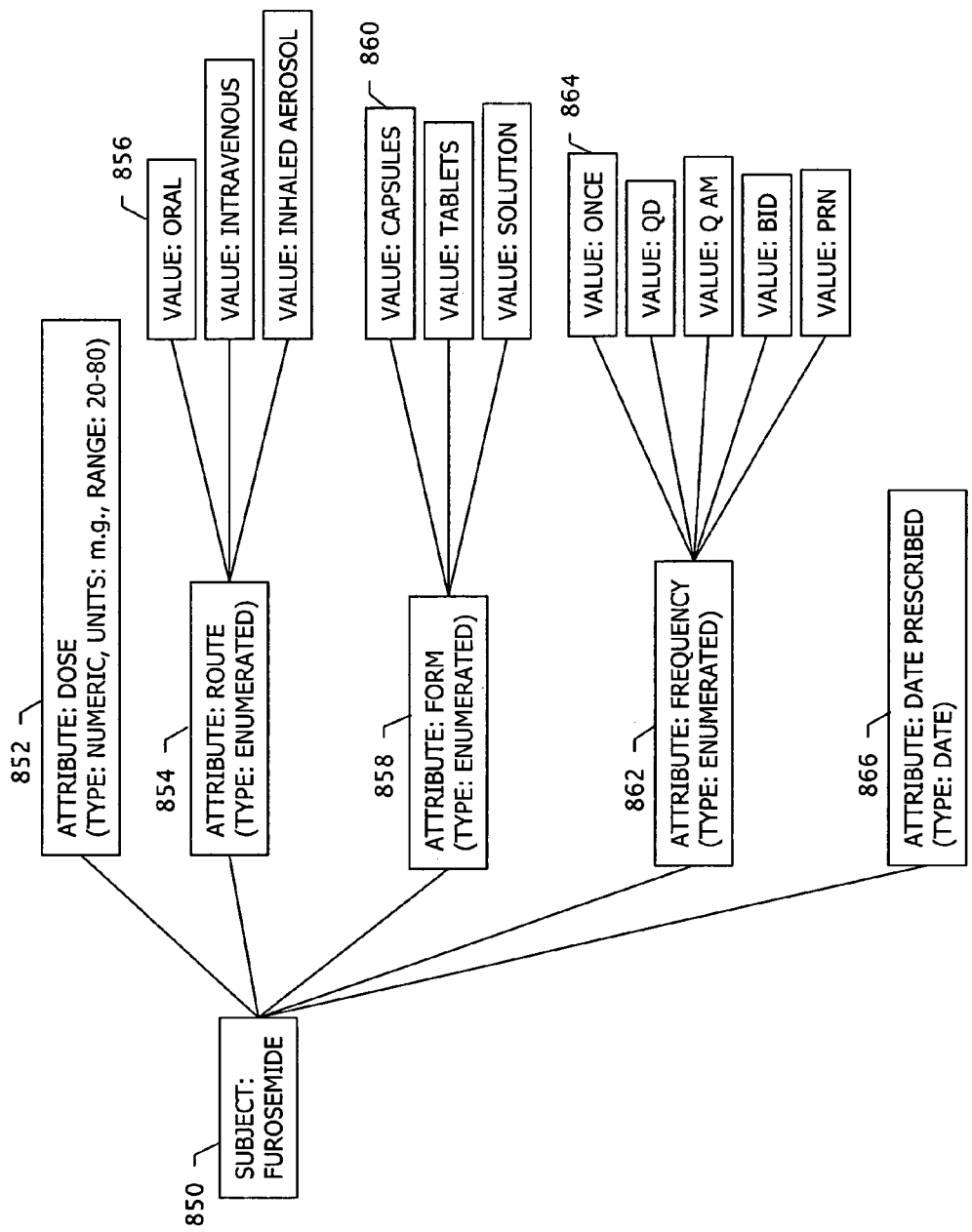
FIG. 5 is a diagram representing an example structured sentence data item.

Turning to FIG. 3, an example of a care plan is provided. The care plan 370 includes a list of the health problems being addressed for the patient 372. For each health problem, the care plan includes a list of the management goals 376, relevant facts 374, the services (health care interventions) 378 that are planned, in progress or already provided for that health problem, and the findings that are associated therewith. In the health care domain, services include diagnostic tests, treatments, referrals to other health care providers, or return visits. Services can also include protocols 382 that describe a logical sequence of other services over time, such as a diagnostic work-up protocol or a cancer treatment protocol. Each of these health problems 372, goals 376, facts 374, services 378, protocols 382, and the findings associated therewith, are preferably created in the health care plan 370 as structured sentence data items, described in more detail below with respect to FIG. 5.

Returning back to FIG. 2, the user, typically the clinician, may electronically route 230 a draft care plan to other members of an inter-disciplinary clinical team to gather their feedback and input to the draft care plan.

Once the draft care plan is finalized, the system instantiates workflow processes in step 220 for each service in the care plan. The instantiation of the workflow processes begins in a manner similar to that for the instantiation of the care plan. The generic workflow specification metadata, which workflow specification metadata is associated with corresponding structured sentences for services, can be edited by a clinician or other user associated with the service provider or new workflow metadata can be created according to preferred specifications to obtain local workflow specification metadata. This workflow specification metadata includes specified tasks which are of task types described in workflow task type metadata. Workflow task type metadata includes information about the data and resources required for a particular workflow task type. As with workflow specification metadata, generic workflow task type metadata can be used "as is," or it can be adapted or created anew by users associated with service provider organizations to meet local needs. Of course, it is understood that the local workflow process specification metadata and local workflow task type metadata can be created in other manners as well.

Using generic and local workflow process specification metadata, the clinician or other user can create workflow process instances associated with the structured sentence. As with the "generic care plan template metadata" discussed above, it is also true that the "generic workflow process specification metadata" is also highly specific with regard to current medical practice as well, and may well be used "as is." Significant to the present invention is the association of a workflow process specification with a particular structured sentence for services, and the ability of the present invention to group structured sentences and associated structured sentences for services together to provide a resulting product that can efficiently track complex interrelationships in the plan.

Thus, the workflow process instances provide the basis for tracking the planning, execution and follow-up of the associated services. When the care plan requires a patient encounter such as a return clinic visit, the system automatically generates 235 an encounter itinerary, describing in a patient understandable report where the patient is to go, what she needs to do to prepare, and what she can expect during the encounter. Whenever new workflow process instances are created corresponding to new services needed based upon new instantiated structured sentences for services being added to the care plan, existing encounter itineraries are automatically re-evaluated and, if necessary, adjusted to optimize the encounters to make them efficient and coordinated for both patients and health care providers. For example, if a patient is already scheduled to come to the medical center in three days, and a test has just been ordered that must be completed within the next week, the test is scheduled to coincide with the scheduled visit if possible.

Each active workflow process instance is executed 225, invoking resources such as clinical staff and automated services as needed according to workflow process specification metadata. The workflow automation server computer (160 from FIG. 1) manages the tracking and execution of these workflow instances.

In addition to supporting the management of the care of individual patients 205, the system also supports the process of population care management, as shown by process 210. More specifically, the user selects, as shown by step 240, a population of patients of interest. The user then analyzes in step 245 data for the selected population in order to gain an understanding of the population and to identify specific needs in the population, including needed services. The user then initiates population interventions in step 250, essentially starting a batch process that updates the individual care plans of the members of the selected population of patients. For example, the clinician can determine that a population of smokers could benefit from a smoking cessation educational intervention and then add that service to the care plan of each smoker who has not already received the service. The execution of the updated care plan is handled by the same process steps 220, 235, 225 used for care plans that are updated on an individual basis.

Another aspect of the present invention illustrated in FIG. 2 is a method for continually improving the metadata based on the performance of a customer service process. The metadata that is improved could be the local metadata for a particular service provider organization, or the generic metadata from the generic metadata supplier. In either instance, based on data generated through the personal care management 205 and population care management 210 processes, the user analyzes in step 255 feedback data on the appropriateness of alerts and suggested plan of care items, as well as data on clinical practice and outcomes to identify opportunities for improvement in the metadata. For example, the user could discover that a particular alert is dismissed as "inappropriate" a large percentage of the time, or a particular service protocol could be found to produce poor health outcomes. Bases on the insights gained through this analysis, the user edits 200 the metadata.

Figure 4:
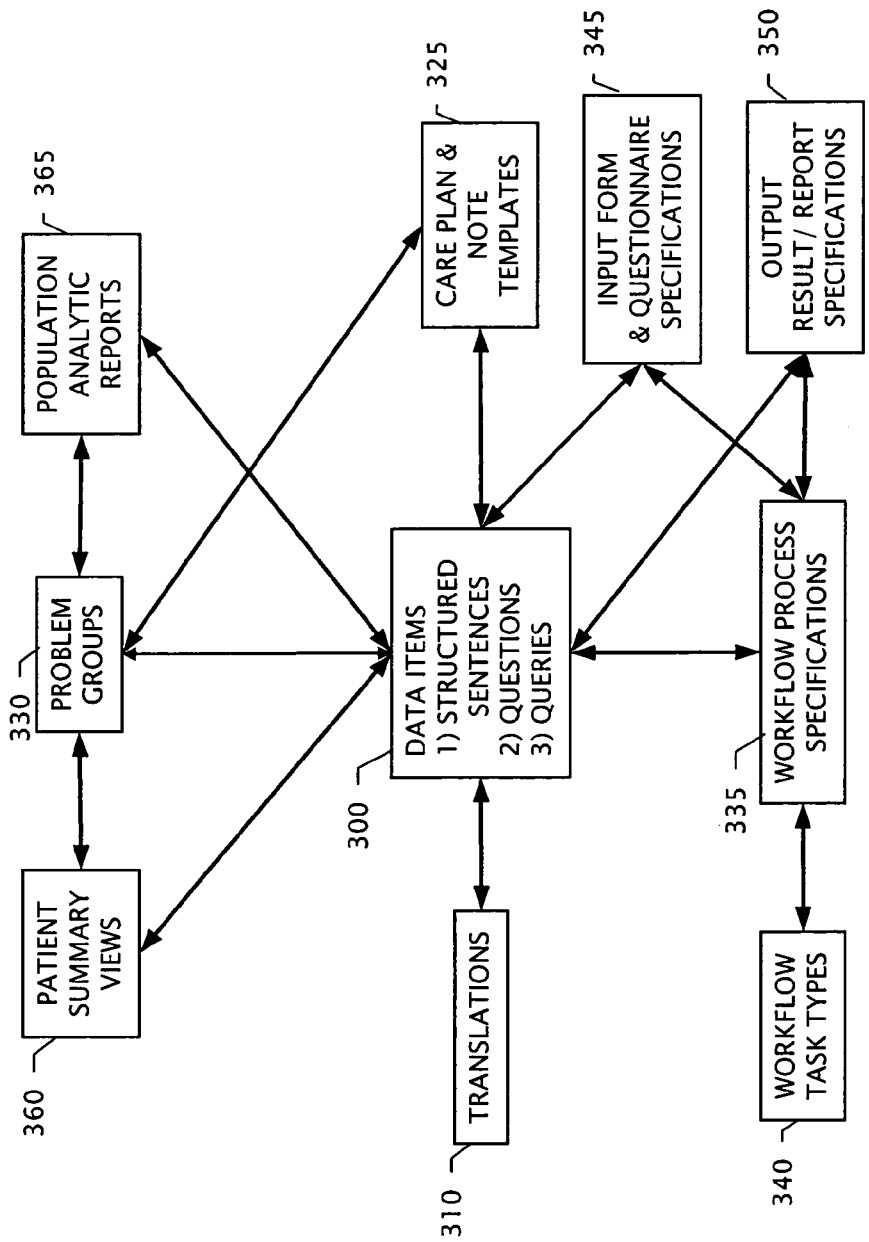
FIG. 4 is a diagram of the relationships between important metadata entities used by the system.

Referring to FIG. 4, the relationships between the various types of metadata are illustrated. Additional FIGS. 5–8 are provided to show examples of some of the metadata types, described below. At the center of this metadata model are data items 300. There are three important types of data items: structured sentences, questions and queries. Structured sentence data items are used to describe health problems being addressed, goals of management, relevant findings, and health care services. Structured sentence data items are comprised of a subject term, and may include one or more attribute terms that modify the subject term. Both subject and attribute terms are of types such as numeric, binary, date, or enumerated. For enumerated (mutually exclusive multiple choice) terms, the term contains a collection of response options (valid values). There preferably is a structured sentence for each different health problem 372, goal 376, fact 374, service 378, protocols 382, and the findings associated therewith as discussed above with respect to the care plan 370 illustrated in FIG. 2. For greater understanding, reference will now be made to FIG. 5, and a specific example of a structured sentence data item for a particular drug is illustrated. The subject 850 identifies the drug as Furosemide. Attributes could include, for example, the dose 852, the route 854, the form 858, the frequency 862, and the date prescribed 866. Other possible attributes, such as the number of refills allowed, the amount of the drug to be dispensed, whether or not the associated prescriptions should be sent to a pharmacy, etc., are not illustrated in FIG. 3A. For the route 854, a collection of valid response options

856 are provided, including oral, intravenous, inhaled aerosol, etc. For the form 858, valid response options 860 include capsules, tablets or solution. For the frequency 862, valid response options 864 include once, QD (daily), Q AM (once a day in the morning), BID (twice a day), PRN (as needed), etc.

Referring to FIG. 6, another type of data item is a question. Questions are used for questionnaires which are administered to patients as part of a protocol to collect baseline history, risk factor and functional status information, or to monitor compliance with treatment advice or outcomes of care. Questions may also be incorporated into data input forms that are completed by users, typically clinical staff, as part of the execution of a care plan. Questions 870 may have explanatory text 872 and one or more data elements 874 and basic layout information, possibly including textual elements and graphical elements 875. Data elements have types. For data elements of type enumerated, the data element includes a collection of response options 876, which may optionally have default values defined. Unlike the attributes in structured sentence templates, the data elements in questions do not necessarily modify the same subject term. In the example, each data element relates in general to difficulty in performing activities, but each describes a different activity. Questions may be designated by the author as being intended to be answered by clinicians (as part of input forms) or patients (as part of questionnaires). The answers provided to questions can then be used to create facts 374 as referenced in the care plan 370 of FIG. 2, to provide needed information for attributes associated with structured sentence data items discussed above, or to provide attributes needed in order to determine workflow routing, determine the state of an alert rule, or the like, as described below. In a preferred embodiment, the patient can remotely enter answers to questions from a customer computer 180 that accesses the computer system associated with the service provider via the Internet.

Referring back to FIG. 4, the third type of data item 300 is queries. Queries provide a way to introduce a layer of abstraction into the authoring of "higher order" metadata including care plan templates, workflow process specifications, etc. Queries return data values based on manipulation of instances of other data items. An example of a query would be a query data item which combined information from a number of related data items, such as a set of data items related to "magnitude of back pain." In this example, the query could map the "very painful" response option in one question item to the "excruciating" response option in a structured sentence item. Once defined, such a query can be used and re-used as if there was a single data item for magnitude of back pain.

Data items are associated with translations 310 to one or more languages or sub-languages, including such sub-languages as "English Medical Terminology," "English Lay Terminology—Educated," and "English Lay Terminology—Simplified." These translations map clinician terminology and abbreviations to patient-understandable versions. For example, the clinical abbreviation "CHF" could be mapped to the complete phrase "congestive heart failure." In addition, the patient-understandable translation for CHF could also include additional explanatory text, such as a description of what are the causes and the common symptoms of congestive heart failure for the example provided above, or a description of the reason that a particular medication is being taken, for example. Thus, in a specific example, the clinical terminology of a medication order of "Lanoxin 0.25 mg QD" could be translated to the following:

"Medication—Lanoxin, which is generically called Digoxin. You are to take one tablet each day. Each tablet contains 0.25 milligrams of the medicine. This medicine helps your heart to pump more strongly."

To accomplish this translation, the associated metadata includes translations at each desired part of the clinical structured sentence, including the subject and the attributes. In addition, the metadata includes additional explanatory text associated with the subject, and patterns for constructing a patient-understandable paragraph from the original clinical structured sentence. In a preferred embodiment, the patient can remotely receive this translation at a customer computer 180 that accesses the computer system associated with the service provider via the Internet.

Figure 7:
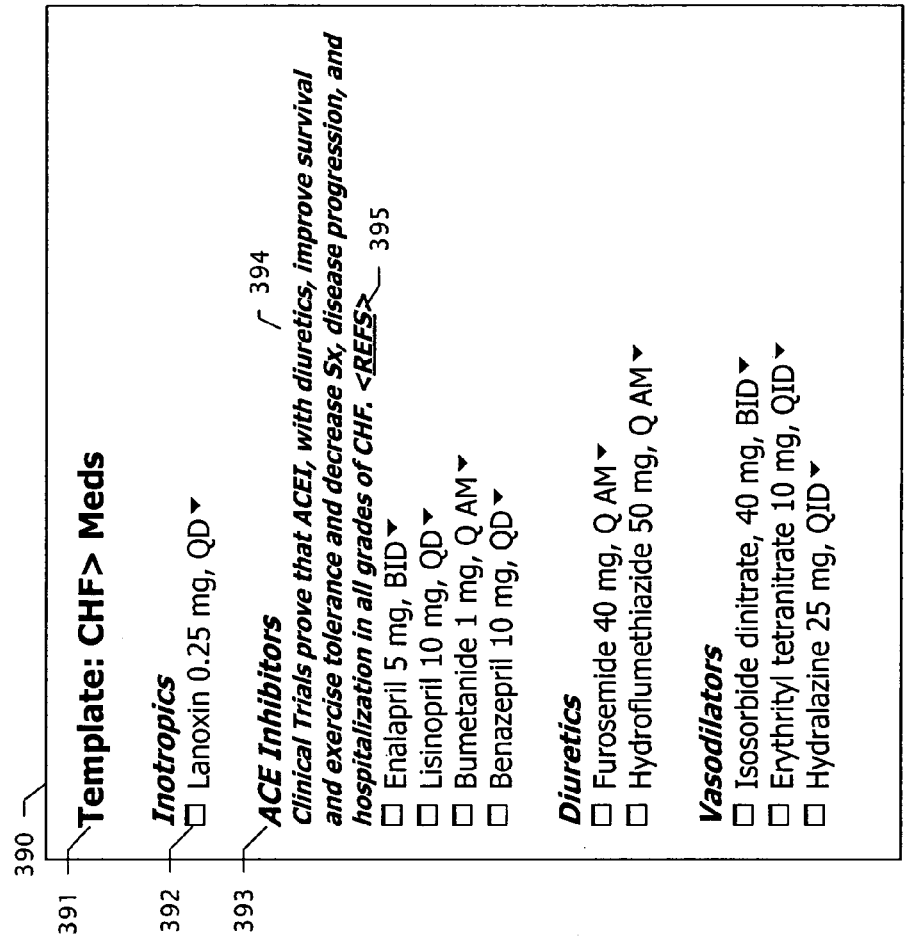
FIG. 7 is a diagram representing an example care plan template.

Care plans are comprised of instances of structured sentences created based on structured sentence data items, as described previously. In order to facilitate rapid, consistent creation of care plans, care plan templates 325 are employed. Care plantemplates are metadata structures which may contain an ordered collection of structured sentence data items, with particular default values assigned, to be incorporated into a care plan as a single interaction, as well as informative headers, groupings, additional information and links to other information sources. Turning to FIG. 7, an example care plan template is provided. In this example the care plan template 390 contains all of the medications usually ordered for patients diagnosed with congestive heart failure, as suggested in header 391. In this template, the individual structured sentence data items 392 refer to specific drugs. In addition, the example template contains informative headers 393, grouping the drugs into drug classes, with additional text 394 providing clinical practice guideline suggestions and a link 395 to additional reference material regarding a drug class. In a preferred embodiment of the system, when a template is selected for inclusion in a patient's care plan, such informative text is presented. Then, when the care plan is subsequently signed, this informative text, as well as any structured sentences with unchecked checkboxes, will be removed from the care plan.

Figure 8:
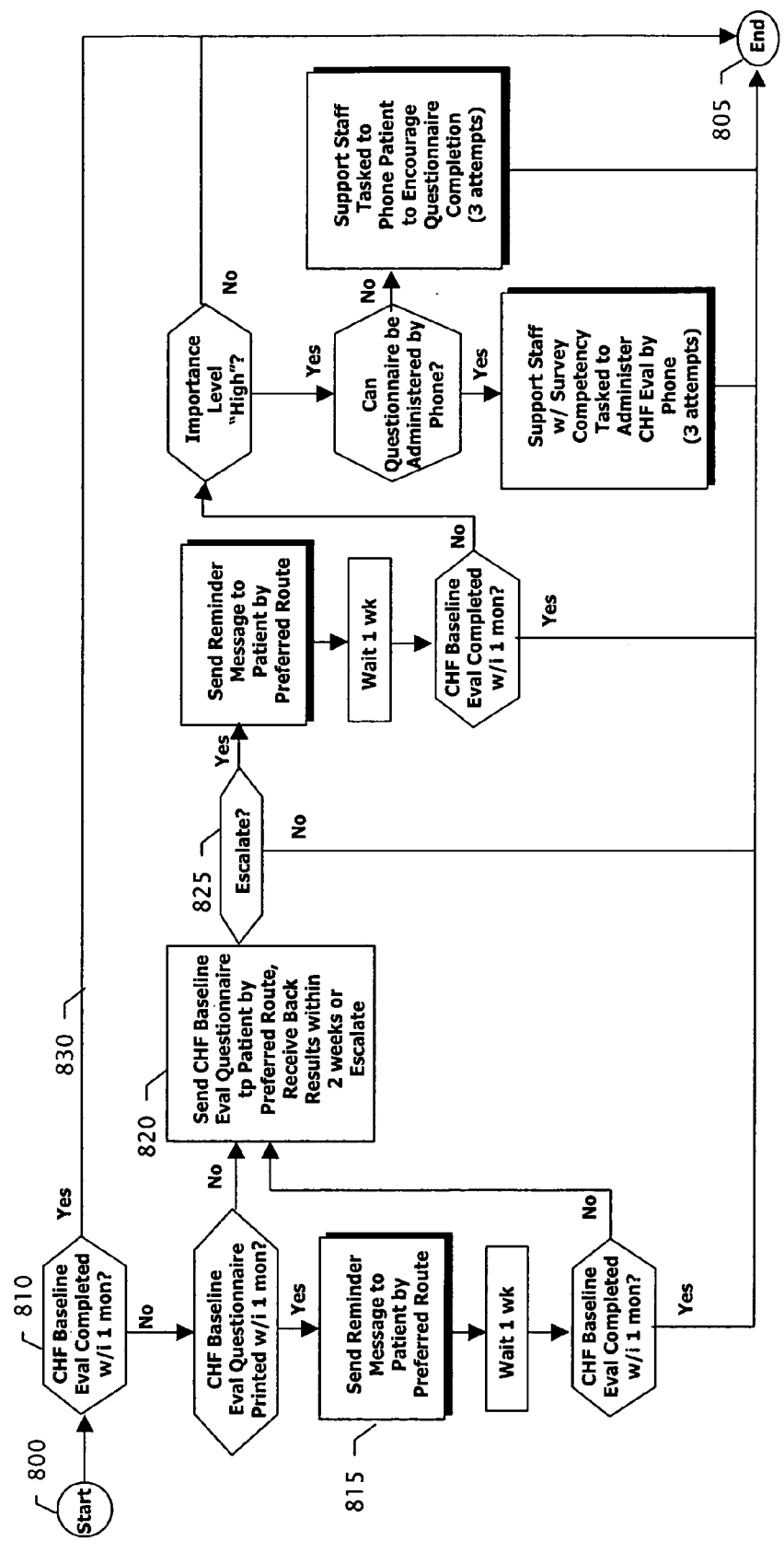
FIG. 8 is a diagram representing an example care process specification.

Returning to FIG. 4, in order to facilitate access to the available care plan templates 325 that relate to a health problem being addressed for a patient, problem group 330 metadata is employed. Each of the structured sentence data items 300 that describe health problems are mapped to problem groups 330 and are stored 155. For example, a group of structured sentence data items for various types of congestive heart failure can be mapped to a problem group of congestive heart failure. The relevant care plan templates 325 are also linked to the problem group, as are other types of metadata, as described below. For example, if the problem "cardiomyopathy" (a type of CHF) were mapped to the problem group "CHF", and then the problem "cardiomyopathy" is included in the care plan for an individual patient, all of the care plan templates related to CHF could be easily accessed. Also referred to in FIG. 4 are "note templates," which provide the user with the capability of including observations at a point in time onto the patient data, such as aspects of the patient's history and physical examination. For each structured sentence data item 300 that relates to a service, a workflow process specification 335 preferably exists that describes the sequence of activities involved in executing the service. Turning to FIG. 8, an example workflow process specification is provided. Workflow process specifications include starting nodes 800, termination nodes 805, tasks 810, 815, 820, 825 (corresponding to the associated activities), and routes 830 (defining the sequence of tasks). Some task nodes 820 refer to specific activities to be performed by a human or system resources specified in the task properties within the workflow specification. Other task nodes 815 refer to sub-processes which are invoked at that point in the parent process. Still other task nodes 810, 825 are decision nodes that determine the logic of the sequence of tasks. It should be noted that different embodiments of the system may use different approaches for determining the logic of tasks. For example, one approach used by workflow automation systems in the art is to use "task firing rules" or "task conditions," which are rules or conditional expressions associated with tasks to determine which tasks or activities are to be invoked at a particular point in time for a particular workflow process instance. In another example, another approach used by workflow automation systems in the art is to use "routing rules," which are rules or conditional expressions associated with the routes connecting tasks to one another. Such rules or conditional expressions determine which routes are to be traversed, thereby determining which tasks or activities to invoke for a particular workflow process instance. The workflow process specification also specifies the data items needed to support both the execution of the tasks and the routing rules.

Referring back to FIG. 4, each task incorporated into a workflow process specification is drawn from a collection of available workflow task types 340. Task type metadata describes what data items are needed for a particular task and the mechanism for invoking the resources required for execution of the task. Task type metadata also includes instructions about the use of the task type. For some tasks within a workflow process specification, additional metadata is needed to describe how to execute the task. For example, if the task is to display a data entry form on the screen to be completed by a clinician or to present a questionnaire to be completed by a patient, input form and questionnaire specification 345 metadata is used, detailing the data items, field validation rules and layout of the form or questionnaire, among other things. In another example, if the task is to post a laboratory result to the database or print a report of patient-specific information, output result/report specification 350 metadata is used, detailing the data items and layout of the result record or report, among other things.

To support the clinician in gaining an overview of the patient's status regarding a particular health problem being addressed, patient summary view 360 metadata describes the layout and underlying data queries needed to summarize patient data related to a problem group 330. To support the clinician gaining and overview of the status of a population of patients with a particular health problem, and to identify needed services for such populations, population analysis report 365 metadata is used to describe the layout and underlying data queries needed to generate appropriate charts, graphs and tables.

Figure 9:
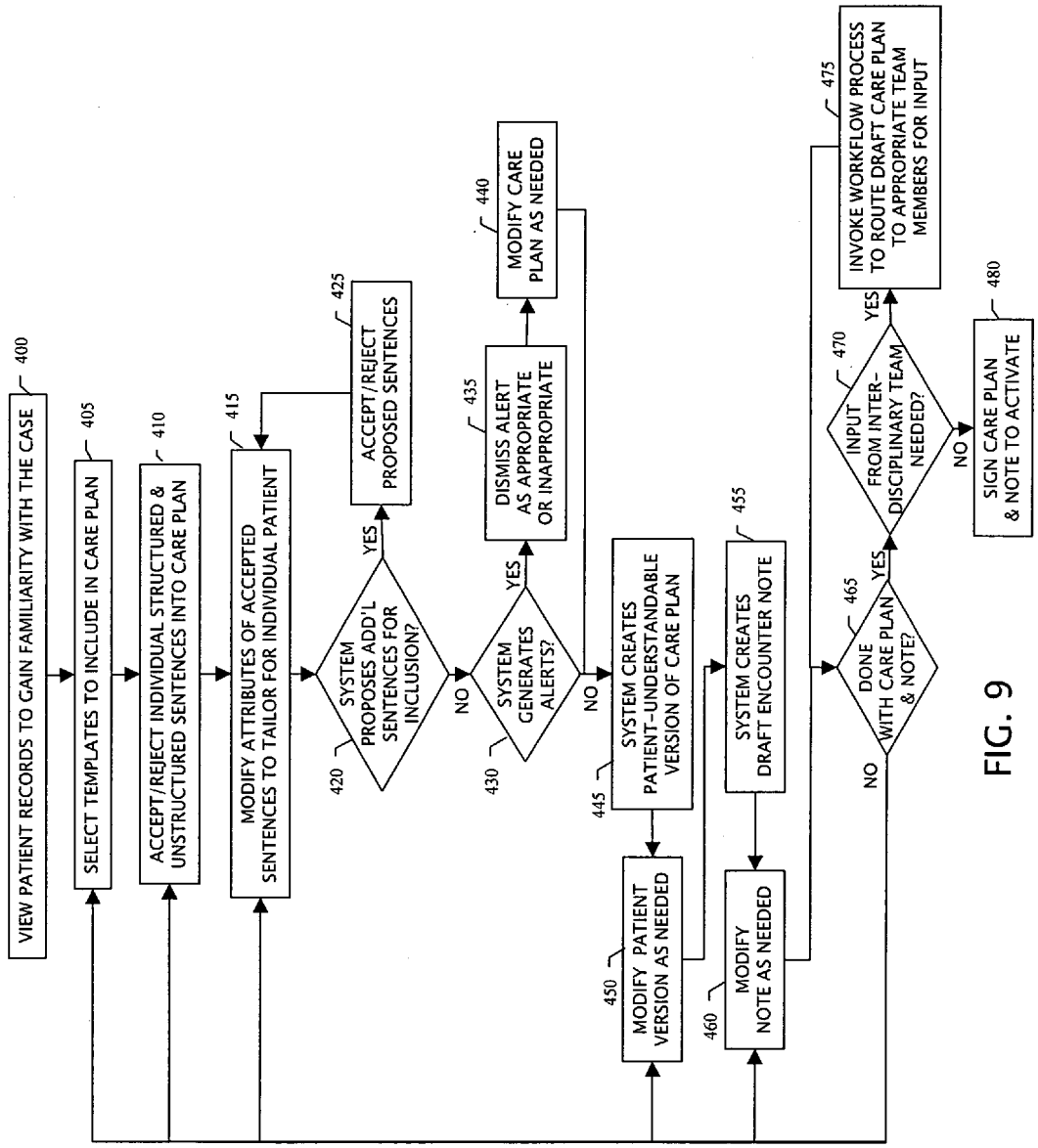
FIG. 9 is process flow diagram providing more detail of the method of creating and updating care plans for individual patients using the system.

Referring to FIG. 9, more detail is provided on the method for creating or editing a care plan for an individual patient (steps 215 and 230 in FIG. 2). This process begins with the clinician user viewing patient records 400 to gain familiarity with the case. Records include the pre-existing care plan, previously created clinical notes (documenting previous patient encounters and procedures), results of tests, consultations, or questionnaires obtained through the execution of pre-existing care process instances, and basic profile information (demographics, insurance information, etc.) entered by the patient or health care providers. Patient summary views summarize the available information related to a particular health problem being addressed for the patient. These records include data stored in the database server computer (150 in FIG. 1), or in external server computers (170 in FIG. 1). Examples of external server computers providing patient information would include a computer serving data from an external electronic medical record, clinical data repository, billing, or managed care application.

The clinician user then selects 405 templates to incorporate into the care plan. The clinician then accepts or rejects 410 the individual structured sentences that have been incorporated into the care plan. The clinician then modifies attributes 415 of accepted sentences to tailor the care plan for the individual patient. Based on user interaction and system events, the system may propose additional sentences 420 for incorporation into the care plan.

Referring back to FIG. 3, an example care plan display in a preferred embodiment of the system illustrates the user interactions involved in care plan creation and editing. Triangle symbols 383 to the right of the care plan header provide a means to call up and select from a list of commonly used or preferred templates. As described above, if structured sentences for health problems have already been entered, care plan templates related to the associated problem group are readily accessible by clicking on triangle symbols 384 to the right of the corresponding problem sentence.

In this example embodiment, structured sentences that have been incorporated into the care plan during the current session are displayed with check-boxes 388, 390, which have default true/false values in the template, and which can be checked or unchecked by the user in the care plan to accept or reject the sentences into the care plan. Unchecked sentences are removed by the system at the conclusion of the user session. The clinician then modifies attributes of accepted sentences by directly clicking on the attribute. In the example, an accepted sentence for a prescription for Enalapril 380 may be modified to change the dosage by clicking on the current dosage "5 mg". The clinician may also add additional attributes by clicking on the triangle symbol 386 to the right of the sentence to reveal a list of available attributes for this structured sentence data item, such as number of pills to dispense, number of allowed refills, etc. Once a given structured sentence data item is selected or checked, that instance of the structured sentence, and the tailored information that has been selected, if any, are saved as part of the care plan for that particular patient.

Referring back to FIG. 9, based on user interaction and system events, the system may propose additional sentences for incorporation into the care plan. For example, if the clinician adds a particular drug to the care plan, the system may propose a monitoring test needed to detect possible adverse effects of the drug on kidney function. In a preferred embodiment, these suggestions are presented as sentences in the care plan with an unchecked check-box with a red exclamation point to the left (shown as 392 in FIG. 3). The clinician then accepts or rejects 425 such proposed sentences.

Based on user interaction and system events, the system may display alerts 430. For example, if the clinician adds a particular drug to the care plan that has an interaction with another drug already in the care plan, the system may generate an alert to that fact. The clinician then views the alert and dismisses the alert 435, and subsequently makes modifications to the care plan 440 as needed. When the clinician dismisses the alert, it is dismissed as an "appropriate alert" or an "inappropriate alert," and this event is recorded in a database. In this manner, the system gathers feedback on alert appropriateness for use in the process 255 of identifying opportunities to improve the metadata related to alerts.

The system automatically generates in step 445 a patient-understandable version of the care plan, with terminology appropriate to the patient's language and preferred sub-language (such as more advanced vs. simpler terminology or culturally-appropriate terminology). This translation is accomplished utilizing translation metadata 310, discussed above. The clinician may view this version and modify the patient-understandable version, as shown by step 450, as needed.

The system also automatically generates in step 455 a draft encounter note, including changes to an existing care plan that result from an encounter. The clinician can modify this note as needed, using note templates metadata or entering free text sentences. In a preferred embodiment, the system accepts voice dictation and either routes the voice data to a transcriptionist or employs voice recognition technology to create a textual version of the material.

It should be noted that, although FIG. 9 portrays the process of selecting, accepting and modifying care plan templates, and modifying the patient version of the care plan and the encounter note in a particular sequence, the preferred embodiment permits these to be done in an order chosen by the clinician user. The clinician continues this process until the care plan and encounter note are complete in step 465. If the clinician determines that input from and inter-disciplinary team is needed, as shown by step 470, then the clinician invokes a workflow automation process 475 to route the draft care plan to appropriate team members for review and input. The routing of the draft care plan is based on workflow process specification metadata (335 in FIG. 4) and is managed by the workflow automation server (160 in FIG. 1). Once this care plan review process is completed, and any needed modifications have been made, the care plan is signed 480 to activate it and commit it to the permanent record for the patient.

In an alternative sequence for this process, the clinician user first invokes a workflow process for interdisciplinary care planning. A task in this workflow process calls for the creation of the draft care plan by one clinician, with subsequent routing to other members of the team for review and input. In this alternative sequence, the entire process of inter-disciplinary care planning is itself a service which can be incorporated into a previous care plan. For example, the care plan for managing a patient with congestive heart failure may call for some tests, some medications, a return visit in 3 months, and an inter-disciplinary review and revision of the care plan in 6 months.

Figure 10:
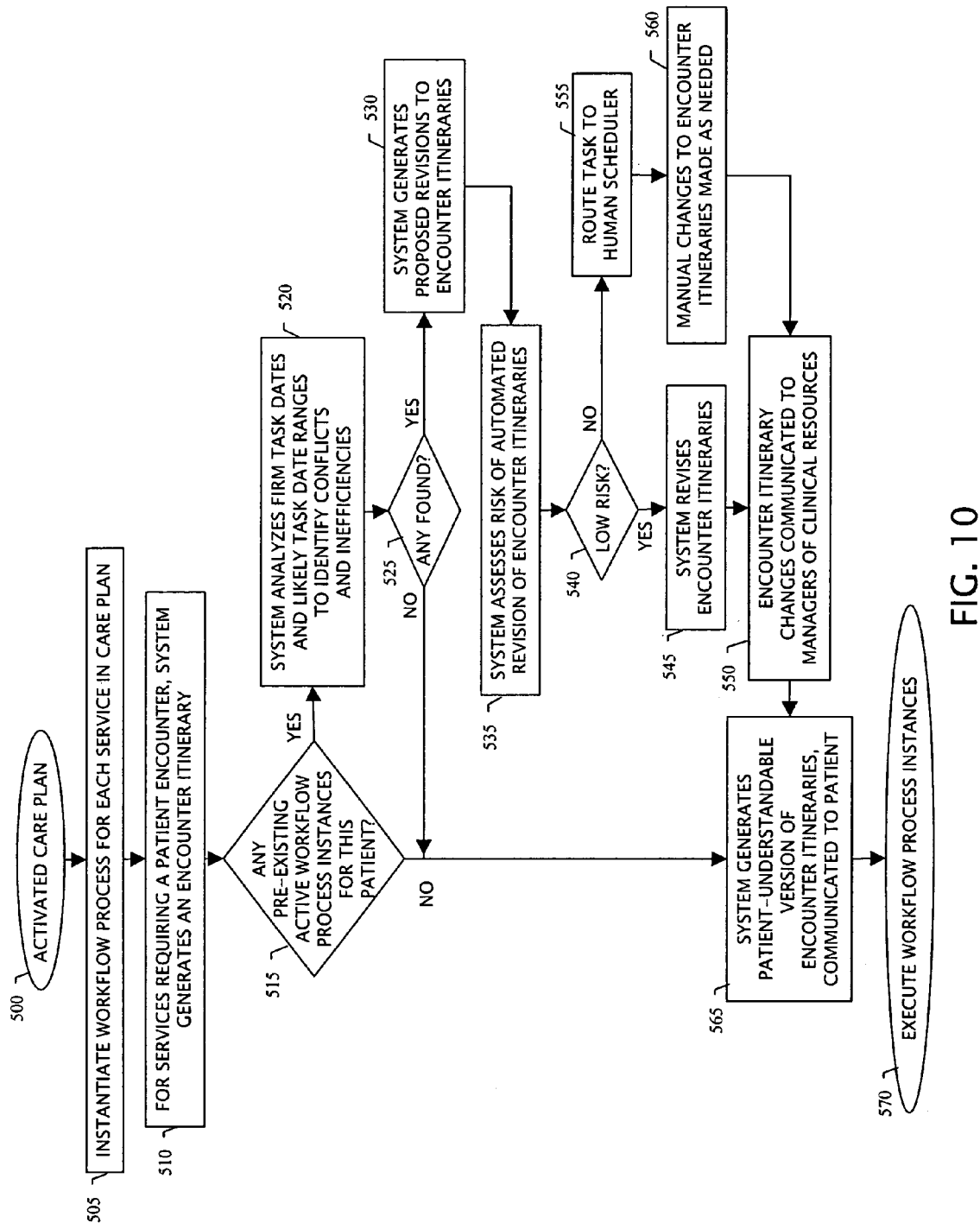
FIG. 10 is a process flow diagram providing more detail of the method of instantiating workflow processes and creating encounter itineraries using the system.

Referring to FIG. 10, more detail is provided on the process for instantiating workflow processes and creating optimized encounter itineraries (220 and 235 in FIG. 2). Beginning with an activated care plan 550 (one that has been electronically signed by an authorized clinician or user), the system instantiates in step 505 at least one workflow process for each service in the care plan. This is accomplished by invoking the workflow automation server (160 in FIG. 1) with reference to a workflow process specification (335 in FIG. 4) corresponding to a data item (300 in FIG. 4) in the care plan which represents a service.

For services in the care plan which require a patient encounter such as a clinic visit, a home health care visit, a hospital admission or a telephone encounter, the system generates in step 510 an encounter itinerary. The encounter itinerary describes the schedule for the encounter and which resources are needed, including clinical staff, facilities, and equipment. The encounter itinerary also contains information about other events that must be completed prior to each event during the encounter. An example of such a dependency would be a scheduled test that must be completed prior to a scheduled treatment. The encounter itinerary includes not only the scheduled times for events in the encounter, but also required time ranges. For example, a treatment may be scheduled for a particular date, but it may be required to be completed any time from one week before to two weeks after the scheduled date. For non-scheduled events, the itinerary data includes an estimate of the likely date range for the event, based on metadata included in the associated workflow process specifications. For example, if a scheduled procedure must be provided after an unscheduled event to complete a mailed pre-procedure questionnaire, the itinerary data for the scheduled event includes an estimate of the likely date range that the questionnaire will be completed, based on elapsed time parameters that are included in the workflow specification for the process of administering the questionnaire.

For newly generated encounter itineraries from step 510, the system follows a method for optimizing the efficiency and convenience of the itinerary, given previously generated itineraries. If there are any pre-existing active workflow instances for the patient identified as a result of decision step 515, the system analyzes in step 520 firm (scheduled) task event dates and like task event dates for unscheduled event to identify "conflicts" and "inefficiences." In this context, a "conflict" is defined as a situation where events a scheduled with an infeasible overlap with another scheduled event. In this context, an "inefficiency" is defined as a situation where events scheduled for multiple encounters could be combined into a single encounter, or events within an encounter could be rescheduled to reduce the overall duration of the encounter.

If any such conflicts or inefficiencies are identified in step 525, the system automatically generates proposed revisions to encounter itineraries in step 130. The system then evaluates the risk in step 535 of automatically accepting the proposed revisions to the encounter itineraries, using pre-determined criteria that is relevant to the risk being analyzed. For example, in one embodiment of this aspect of the invention, the system could judge as high risk any changes that require the patient to come to the clinic on a different day, or earlier on the same day, while judging as low risk changes that shorten the duration of an encounter or eliminate the need for an encounter that had been scheduled near to another encounter. If the risk of automatic itinerary revision is calculated to be low in decision step 540, the system revises the encounter itineraries in step 545 and these changes are communicated in step 550 to the managers of the clinical resources involved. If, on the other hand, the risk of automatic itinerary revision is calculated to be high in decision step 540, the system routes a task in step 555 to a human scheduler to review the itineraries, the identified conflicts or inefficiencies, and the proposed changes for consideration. This person makes manual changes, as shown by 560, to the encounter itineraries as needed.

In either case, the system then generates in step 565 a patient-understandable version of any encounter itineraries that were created or revised and communicates these to the patient. The patient-understandable version is translated to use terminology appropriate to the patient's preferred language or sub-language (such as English—Lay Person Educated vs. English—Lay Person Simple). It is also augmented with information regarding what they need to do to prepare for the encounter, how to get to the encounter, and what to expect, as well as links to related educational materials. For example, if the patient is scheduled to undergo an outpatient surgical procedure, the patient version of the encounter itinerary could include information about the procedure and about the anesthesia likely to be used.

The entire collection of active workflow process instances for the patient are then executed in step 570, as described below.

Figure 11:
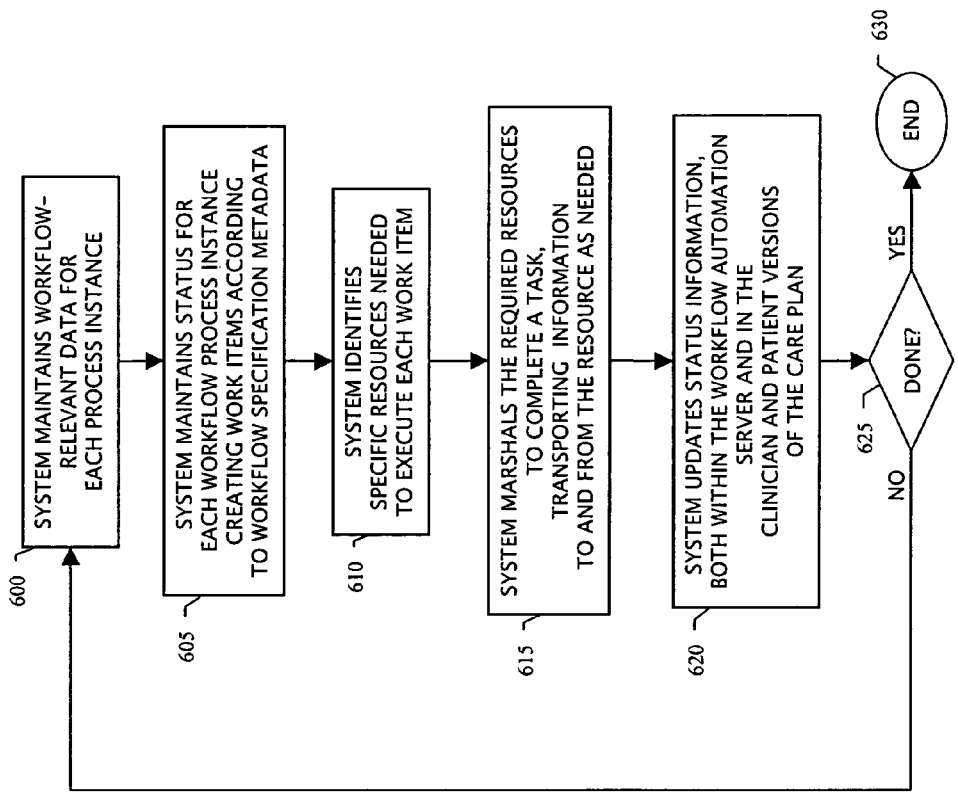
FIG. 11 is a process flow diagram providing more detail of the method of executing workflow process instances using the system.

Referring to FIG. 11, more detail is provided regarding the method for executing workflow process instances (220 in FIG. 2). This process is managed by the workflow automation server computer (160 in FIG. 1) using workflow specification metadata (335 in FIG. 4). The workflow automation server maintains workflow relevant data for each process instance, as shown by initial state 600. In this context, workflow relevant data includes data needed to control the sequence of tasks and to instantiate work items for each task. Workflow relevant data includes the attributes and values of the structured sentence for a service which was associated with the workflow process instance. Workflow relevant data can also include data accessed, created or modified as part of the execution of the workflow process instance, such as through queries to service customer data, queries to external server computers, the completion of questionnaires and data input forms by users, execution of computer logic, and other activities or events. Based on this workflow relevant data, the system maintains status as shown by step 605 for each workflow process instance, creating work items according to workflow specification metadata. In the art, this is described as a "coordination service" within the workflow automation server. For each work item, the system identifies specific resources needed to execute each work item, including human resources and system resources, as shown by step 610. The workflow specification metadata 335 may directly dictate the specific resource required. Alternatively, in a preferred embodiment, the workflow specification metadata specifies a "role" or criteria for determining which of the available resources is best suited for the task. A separate service, described as an "organization service" in the art, handles the process of identifying the specific resource to be utilized.

Once the resources required for a work item are identified, the system marshals the required resources, communicating information to and from the resource as needed in step 615. This process is described in the art as a "transport service," and can be carried out by the workflow automation server 160, or, in a preferred embodiment, by a separate server computer dedicated to that purpose.

The system then updates the status information in step 620, both within the workflow automation server and in the clinician and patient versions of the care plans. Within the care plan, this is achieved by adding or modifying attributes of the structured sentences in the care plan, or adding one or more new structured sentences relating to the status of the services in the care plan. This process of updating the status information displayed in the clinician and patient versions of the care plan can be done proactively (on a "push" basis), as status changes within the workflow automation server. Alternatively, in a preferred embodiment, the up-to-the-minute status information can be communicated outside the workflow automation server at the time that a user chooses to view the care plan (on a "pull" basis). The workflow automation server continues to manage the execution of each workflow process instance, using a decision step 625, until it has reach a status of completed (or until it is terminated by an authorized user), at which point the process ends 630.

Figure 12:
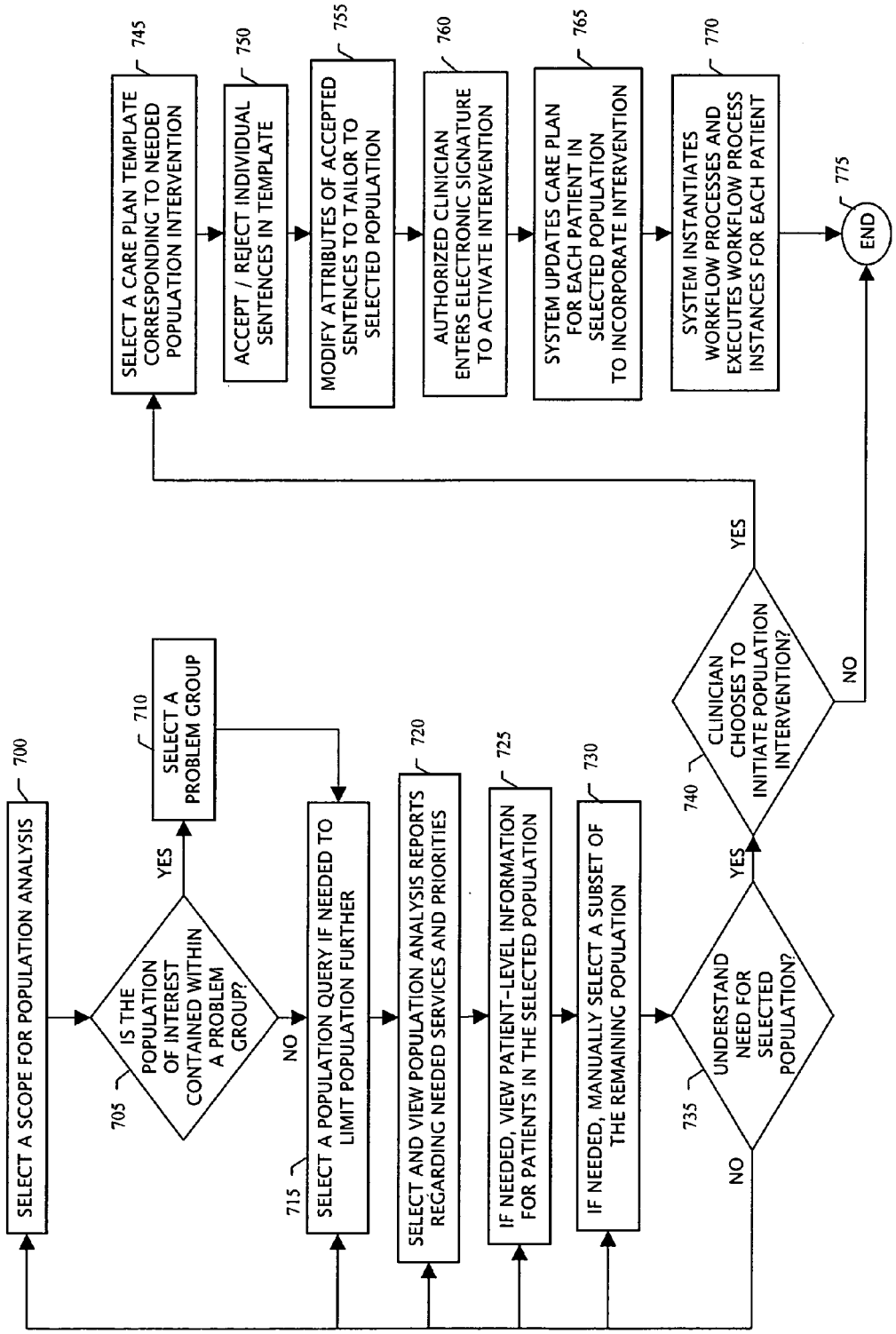
FIG. 12 is a process flow diagram providing more detail of the method of population care management using the system.

Referring to FIG. 12, more detail is provided regarding the method for population care management (210 in FIG. 2). According to the preferred embodiment of this method, the clinician user first selects a scope for population analysis in step 700. Examples of alternate scopes include "my panel," "my clinic" or "my institution." Then, the clinician determines in step 705 if the population of interest is described by, or contained within the population of patients for which their care plan includes a health problem that has been mapped to a particular problem group. In most cases, this is likely to be true, since the problems groups are defined so as to group patients with similar care plan requirements together. If so, the clinician selects in step 710 a problem group of interest to further constrain the selected population within the selected scope.

In any case, the clinician may then decide to further constrain the selected population using a population query shown by step 715. A population query is metadata defining patient selection criteria. For example, a population query could define the subset of patients who are in a high risk category, or the subset who do not have a particular service included in their care plan. In a preferred embodiment, the clinician may layer population queries on top of one another or define new patient selection criteria on an ad hoc basis.

Having refined the selection of a population of interest, the clinician may then select and view population analysis reports regarding needed services and priorities, as shown by step 720. These population analysis reports are displayed based on population analysis report metadata (365 in FIG. 4). In a preferred embodiment, the clinician may select from available pre-defined reports, or define a new report on an ad hoc basis.

If needed, the clinician may view patient-level information for patients within the selected population. In a preferred embodiment, a table listing the individual patients in the selected population is displayed, with columns filled with data items relevant to the selected problem group. The patient name is the table is implemented as a hypertext link to the patient's chart, specifically to a patient summary view for the problem group selected. In this embodiment, the problem-oriented patient summary view would be generated based on patient summary view metadata (360 in FIG. 4).

If needed, the clinician may also manually select a subset of patients within the previously selected population. In a preferred embodiment, this is accomplished with a check-box user interface included as one of the columns in the table view described above.

The clinician continues to refine the population selection and analyze selected populations until the clinician understands the services that may be needed for a selected population, as shown by step 735. It should be noted that, although this population selection and analysis process is presented in FIG. 12 in a particular sequence, a preferred embodiment would allow the clinician to choose the order of the these steps in an iterative fashion.

Then, if the clinician chooses to initiate a population intervention in step 740, the clinician selects one or more care plan templates in step 745 corresponding to the needed population intervention. As with the process of creating and updating care plans for individual patients, the clinician then accepts or rejects individual sentences in the selected template(s) in step 750. The clinician then modifies the attributes of accepted sentences in step 755 to tailor the care plan fragment to the selected population. An authorized clinician then enters and electronic signature in step 760 to activate the population intervention. The system then updates the care plan for each patient in the selected population to incorporate the sentences in the signed care plan fragment (describing the population intervention) in step 765. Subsequently, the system instantiates in step 775 at least one workflow process for each new service in the updated care plans, and executes these workflow process instances using the same method and system components as with care plan updates made for individual patients, as described on a general level in FIG. 2 (steps 220, 235, 225), and in detail in FIG. 5 and FIG. 6.

Although the above description contains many specificities, these should not be construed as limitations on the scope of the invention, but merely as illustrations of the presently preferred embodiment. Many other embodiments of the invention are possible. For instance, it was mentioned that the present invention can be used in environments other than the specific embodiment of health care discussed above. In such other environments, the service plan can be viewed as the care plan discussed above, the customer can be viewed as the patient discussed above and the specific service provider user can be viewed as the user or clinician discussed above. The specific types of structured sentences, particularly structured sentences for services and related workflows, both in terms of metadata and instantiated data, will exist and be unique for that type of service provider's business, but will nonetheless be correlated in the same manner as described above. Therefore, the scope of the invention should be determined, not by examples given, but by the appended claims and their legal equivalents.

What is claimed is:

1. A method for generating a service plan that describes a plurality of services and associated workflow for a customer using a computer based system comprising the steps of:

creating the service plan, the service plan including a plurality of structured sentences for each of a plurality of specific needs of a particular customer in an electronic storage area, wherein some of said plurality of structured sentences have a subject and an attribute contained therein, wherein the plurality of structured sentences together form a part of the service plan, said plurality of structured sentences including structured sentences for services, each structured sentence for service identifying a needed service corresponding to one of the specific customer needs;

creating the electronic workflow in addition to the service plan, which is adapted to assist in providing each needed service, the step of creating the electronic workflow including the step of using certain ones of said structured sentences for service to create a workflow process instance for each needed service, wherein at least certain ones of the workflow process instances include a plurality of tasks corresponding to steps for providing one of the services to the particular customer, which one service relates to the corresponding structured sentence for service; and electronically inputting answers to questions, wherein the electronically input answers to questions also causes a change to the one sequence invoked within the one workflow process instance, and wherein the step of electronically inputting answers to questions is performed by the customer.

2. A method according to claim 1 wherein the step of electronically inputting answers includes the steps of the customer remotely answering questions and transmitting the questions for inputting via the Internet.

3. A method according to claim 1 wherein certain ones of said plurality of workflow process instances have workflow relevant data contained therein.

4. A method according to claim 3 further including the step of electronically inputting answers to questions, and wherein the electronically input answers to questions are used to create or modify workflow relevant data for certain ones of the workflow process instances.

5. A method for generating a service plan that describes a plurality of services and associated workflow for a customer using a computer based system comprising the steps of:

creating the service plan, the service plan including a plurality of structured sentence for each of a plurality of specific needs of a particular customer in an electronic storage area, wherein some of the structured sentences have a subject and an attribute contained therein, wherein certain of the attributes associated with the structured sentences contain a selected attribute value chosen from among a group of possible attribute values, and wherein the plurality of structured sentences together form a part of the service plan, said plurality of structured sentences including structured sentences for services, each structured sentence for service identifying a needed service corresponding to one of the specific customer needs;

creating the electronic workflow in addition to the service plan, which is adapted to assist in providing each needed service, the step of creating the electronic workflow including the step of using certain ones of said structured sentences for service to create a workflow process instance for each needed service, wherein at least certain ones of the workflow process instances include a plurality of tasks corresponding to steps for providing one of the services to the particular customer, which one service relates to the corresponding structured sentence for service;

wherein the certain ones of said workflow process instances have at least one decision step, task firing condition or routing rule that creates a plurality of possible sequences of tasks, one sequence of which becomes the plurality of tasks invoked as part of a further step of executing one of said workflow process instances, and wherein the step of executing the workflow process instance includes the step of invoking and executing pre-existing query data items, thereby causing workflow relevant data to be created or modified, said query data items containing metadata that maps response options in a question or structured sentence data item to other response options in at least one other question or structured sentence data item, thereby creating a single data value used in a decision step, task firing condition or routing rule as part of the execution of said workflow process instance.

6. A method for generating a service plan that describes a plurality of services and associated workflow for a customer using a computer based system comprising the steps of:

creating the service plan, the service plan including a plurality of structured sentences for each of a plurality of specific needs of a particular customer in an electronic storage area, wherein the plurality of structured sentences together form a part of the service plan, said plurality of structured sentences including structured sentences for services, each structured sentence for service identifying a needed service corresponding to one of the specific customer needs; and creating the electronic workflow in addition to the service plan, which is adapted to assist in providing each needed service, the step of creating the electronic workflow including the step of using certain ones of said structured sentences for service to create a workflow process instance for each needed service, wherein at least certain ones of the workflow process instances include a plurality of tasks corresponding to steps for providing one of the services to the particular customer, which one service relates to the corresponding structured sentence for service, wherein the steps of creating are repeated to result in a plurality of existing service plans corresponding to a respective plurality of customers, each of said existing service plans including a plurality of structured sentences for each of a plurality of specific needs of a particular customer, each of said plurality of existing service plans stored in an electronic storage area, said plurality of structured sentences in each of said existing service plans including structured sentences for services, each structured sentence for service in each of said existing service plans identifying a needed service corresponding to one of the specific needs of a particular customer, and each of said existing service plans having associated therewith an existing electronic work flow that is in addition to said existing service plan and is capable of assisting completion of each needed service;

identifying one or more needed services in addition to those services specified in the existing service plans;

identifying certain of the plurality of customers in need of the one or more identified services;

automatically adding new structured sentences for service that are common to certain of the plurality of existing service plans for the selected certain plurality of customers to obtain a certain corresponding plurality of revised service plans;

automatically adding workflow process instances corresponding to the new structured sentences for service to the existing electronic workflow for each of the selected certain plurality of customers to obtain a revised electronic workflow for each of the selected certain plurality of customers; and causing initiation of the revised workflow for each revised service plan.

7. A method according to claim 6 wherein said plurality of new structured sentences have a subject and a plurality of attributes contained therein and wherein the step of adding new structured sentences includes the step of determining values for certain of said plurality of attributes for said new structured sentences based upon a characteristic that is common to each of said certain plurality of customers.

8. A method according to claim 7 wherein the step of automatically adding new structured sentences includes the step of determining values for other ones of said plurality of attributes for said new structured sentences based upon another characteristic that is not common for each of said certain plurality of customers.

9. A method according to claim 6 wherein the step of automatically adding new structured sentences further includes the step of modifying certain existing structured sentences that are common to the predetermined plurality of existing service plans based upon the data; and wherein the step of automatically adding workflow instances includes the step of revising workflow instances associated with the modified certain existing structured sentences.

10. A method for generating a service plan that describes a plurality of services and associated workflow for a customer using a computer based system comprising the steps of:

creating the service plan, the service plan including a plurality of structured sentences for each of a plurality of specific needs of a particular customer in an electronic storage area, wherein the plurality of structured sentences together form a part of the service plan, said plurality of structured sentences including structure sentences for services, each structured sentence for service identifying a needed service corresponding to one of the specific customer needs;

creating the electronic workflow in addition to the service plan, which is adapted to assist in providing each needed service, the step of creating the electronic workflow including the step of using certain ones of said structured sentences for service to create a workflow process instance for each needed service, wherein at least certain ones of the workflow process instances include a plurality of tasks corresponding to steps for providing one of the services to the particular customer, which one service relates to the corresponding structured sentence for service; and updating metadata, said metadata including structured sentence data items that are usable for the creation of service plans for particular customers and generic workflow process specifications that are adapted for the creation of work flow process instances used to assist in providing a service to particular customers, said plurality of structured sentence data items including structured sentence data items for services, each structured sentence data item for service identifying a possible needed service corresponding to a possible customer need, and each said associated workflow process specification including workflow data describing a plurality of tasks, routes, decision steps, task firing conditions and routing rules that are capable of assisting completion of one of the needed services and including an alert to signify that an action needs to be taken with respect to the one of the needed services, the step of updating metadata including the steps of:

displaying alert messages according to logic within workflow process specifications;

dismissing identified alert messages in response to a user input, the step of dismissing identified alert messages including the steps of dismissing the message as one of appropriate and inappropriate, and capturing data relating to the identified alert messages and which alert messages were subsequently dismissed as appropriate or inappropriate;

automatically aggregating the data to identify workflow process specifications with alert logic that causes dismissal of alert messages as inappropriate a determined proportion of the time; and determining revised generic workflow process specifications and revised structured sentences data items based upon the identification obtained from the step of automatically aggregating.

11. The method according to claim 10 wherein the step of automatically aggregating is performed for the data associated with a plurality of customers.

12. An apparatus for generating a service plan and associated electronic workflow for a customer comprising:

means for creating, in an electronic storage area, the service plan for the customer, the service plan including a plurality of structured sentences for each of a plurality of specific customer needs of customers, said plurality of structured sentences including structured sentences for services, each structured sentence for service identifying a needed service corresponding to one of the specific customer needs, and wherein certain ones of said plurality of structured sentence have a subject and an attribute contained therein means for creating the electronic workflow, the electronic workflow being in addition to the service plan, and capable of assisting completion of each needed service, the means for creating including means for using certain ones of said structured sentences for service to create a workflow process instance for each needed service, wherein at least certain ones of the workflow process instances include a plurality of tasks corresponding to steps for providing one of the services to the particular customer, which one service relates to the corresponding structured sentence for service; and means for electronically inputting answers to questions, and wherein the electronically input answers to questions also causes a change to the sequence of tasks invoked within at least one of the workflow process instances wherein the means for electronically inputting answers to questions is operated by the customer.

13. An apparatus according to claim 12 wherein the means for electronically inputting answers includes means for the customer to remotely answer questions and means for transmitting the questions for inputting via the Internet.

14. An apparatus according to claim 12 wherein certain ones of said plurality of workflow process instances have workflow relevant data contained therein and further including means for electronically inputting answers to questions, and wherein the electronically input answers to questions are used to create or modify workflow relevant data for certain ones of the workflow process instances.

15. An apparatus for generating a service plan and associated electronic workflow for a customer comprising:

means for creating in an electronic storage area, the service plan for the customer, the service plan including a plurality of structured sentences for each of a plurality of specific customer needs of customers, said plurality of structured sentences including structured sentences for services, each structured sentence for service identifying a needed service corresponding to one of the specific customer needs and wherein certain ones of said plurality of structured sentences have a subject and at least one attribute contained therein wherein certain of the attributes associated with the structured sentences for services contain a selected attribute value chosen from among a group of possible attribute values, and wherein certain ones of said workflow process instances have at least one decision step, task firing condition or routing rule that create a plurality of possible sequences of tasks that are invoked as part of the execution of said workflow process instances;

means for creating the electronic workflow, the electronic workflow being in addition to the service plan, and capable of assisting completion of each needed service, the means for creating including means for using certain ones of said structured sentences for service to create a workflow process instance for each needed service, wherein at least certain ones of the workflow process instances include a plurality of tasks corresponding to steps for providing one of the services to the particular customer, which one service relates to the corresponding structured sentence for service; and means for invoking and executing pre-existing query data items, thereby causing workflow relevant data to be created or modified, said query data items containing metadata that maps response options in a question or structured sentence data item to other response options in at least one other question or structured sentence data item, thereby creating a single data value used in a decision step, task firing condition or routing rule as part of executing said workflow process instance.

16. An apparatus according to claim 15 further including means for creating other structured sentences, said other structured sentences including structured sentences for a goal, a fact, a protocol, and a finding.

17. A method for creating a service plan and associated workflow for a particular customer using a computer based system comprising the steps of:

providing electronically:
a plurality of structured sentence data items for each of a plurality of possible customer needs in an electronic storage area said plurality of structured sentence data items including structured sentence data items for services, each structured sentence data item for service identifying a needed service responding to one of the possible customer needs;

a generic electronic workflow process specifications in addition to the plurality of structured sentence data items, that is adapted to assist completion of each needed service; and at least first and second templates, each of said at least first and second templates comprising a different set of certain ones of said plurality of structured sentence data items different ones of said plurality of structured sentence data items relating to different possible customer needs;

selecting at least a first template that relates to an identified customer need;

creating the service plan for the particular customer, the step of creating the service plan including the step of selecting structured sentence data items within the first template that relate to a specific need of the particular customer to obtain the service plan for the particular customer with structured sentences therein corresponding to the selected structured sentence data items, the structured sentences in the service plan being in addition to the selected structured sentence data items, and wherein the step of selecting structured sentence data items also causing the selection of workflow instances including the step of determining a value for the at least one attribute for certain ones of the selected structured sentences in the service plan for the particular customer, wherein the step of selecting the structured sentence data items also includes the steps of:

visually displaying certain ones of the structured sentence data items on a screen of a display; and creating one structured sentence corresponding to the specific need of the particular customer by selecting one of the displayed certain ones of the structured sentence data items;

creating the workflow in addition to the service plan using the generic workflow specification and the service plan, the workflow being adapted to assist completion of each needed service, wherein the step of creating the workflow includes the step of using certain ones of said structured sentences for service to create a workflow process instance for each needed service;

displaying the one structured sentence on the screen of the display after the step of creating the one structured sentence corresponding to the specific need of the particular customer, wherein the one structured sentence displayed on the screen resembles a substantially grammatically correct phrases and wherein the one structured sentence displayed on the screen contains information obtained from a subject of the selected one of the displayed certain ones of the structured sentence data items and a selected value corresponding to an attribute associated with the selected one of the displayed certain ones of the structured sentence data items.

18. A method according to claim 17 wherein the attribute for certain ones of said plurality of attributes is a dosage.

19. A method according to claim 17, wherein the service plan is a care plan, the customer is a patient, the plurality of possible customer needs are health related problems, and the specific need of the particular customer is a health related problem of the particular customer.

20. A method according to claim 17 further including the step of initiating the workflow, the step of initiating the workflow being caused by a user verifying the accuracy of the service plan.

21. A method according to claim 17 wherein the plurality of structured sentences data items in at least one of said first and second templates include a group of structured sentences data items that are associated with a customer need.

22. The method according to claim 17 wherein the certain ones of the structured sentence data items displayed on the screen resemble a substantially grammatically correct phrase.

23. The method according to claim 17 wherein:
the step of visually displaying includes the step of visually displaying attributes of one of the certain ones of the structured sentence data items; and
the step of creating the one structured sentence corresponding to the specific need of the particular customer includes selecting a selected value obtained from one of the attributes.

24. The method according to claim 23 wherein the step of creating further includes creating one workflow process instance that corresponds to the one structured sentence.

25. The method according to claim 17 wherein at least certain ones of the workflow process instances including a plurality of tasks corresponding to steps for providing one service to the particular customer, which one service relates to the corresponding structured sentence for service.

26. The method according to claim 25 further including the step of executing the workflow, the step of executing the workflow including tracking a status of each workflow process instance through the plurality of tasks as required to assist in execution and follow-up of the one service.

27. The method according to claim 17 wherein the plurality of structured sentences, including structured sentences for service, in service plan, are displayed together to the user with the appearance of a textual document.

28. The method according to claim 27 further including the step of creating other structured sentences, said other structured sentences including structured sentences for a goal, a fact, a protocol, and a finding.

29. The method according to claim 17 wherein the step of creating the workflow includes the steps of:
activating the service plan; and
using the activated service plan to create the workflow from the generic workflow specification.

30. The method according to claim 29 further including the steps of:
initiating the workflow; and
executing the workflow.

31. The method according to claim 17 wherein a separate electronic record is maintained for each of the templates, the generic workflow specification, the service plan for each of a plurality of customers, and the workflow for each of the plurality of customers.

32. A method for creating a service plan and associated workflow for a particular customer using a computer based system comprising the steps of:
providing electronically:
a plurality of structured sentence data items for each of a plurality of possible customer needs in an electronic storage area, said plurality of structured sentence data items including structured sentence data items for services each structured sentence data item for service identifying a needed service corresponding to one of the possible customer needs;
a generic electronic workflow process specification, in addition to the plurality of structured sentence data items, that is adapted to assist completion of each needed service; and
at least first and second templates, each of said at least first and second templates comprising a different set of certain ones of said plurality of structured sentence data items, different ones of said plurality of structured sentence data items relating to different possible customer needs;
selecting at least a first template that relates to an identified customer need;
creating the service plan for the particular customer, the step of creating the service plan including the step of selecting structured sentence data items within the first template that relate to a specific need of the particular customer to obtain the service plan for the particular customer with structured sentences therein corresponding to the selected structured sentence data items, the structured sentences in the service plan being in addition to the selected structured sentence data item and wherein the step of selecting structured sentence data items also causing the selection of workflow instances includes the step of determining a value for the at least one attribute for certain ones of the selected structured sentences in the service plan for the particular customer, wherein the step of obtaining the service plan with structured sentences therein includes the steps of:
creating a structured sentence in the service plan for certain ones of the structured sentence data items selected from the template wherein the step of creating the structural sentence includes the steps of:
creating a structured sentence subject based on the subject in the corresponding structured sentence data item,
creating a structured sentence attribute based on the attribute in the corresponding structured sentence data item, and
settings a structured sentence attribute value based on a default attribute value specified in the corresponding attribute of the corresponding structured sentence data item;
creating the workflow in addition to the service plan using the generic workflow specification and the service plan, the workflow being adapted to assist completion of each needed service, wherein the step of creating the workflow includes the step of using certain ones of said structured sentences for service to create a workflow process instance for each needed service; and changing the structured sentence attribute value for at least one attribute for at least one structured sentence in the service plan from the default attribute value to a selected attribute value, wherein the step of changing the structured sentence attribute value includes the step of displaying a list of possible attribute values specified for the corresponding attribute of the structured sentence data item; and selecting one of the possible attribute values from the displayed list as the selected attribute value.

33. The method according to claim 32 wherein the step of using each structured sentence for service to create the workflow process instance include the steps of:
matching the structured sentence to a corresponding workflow process specification;
creating a new workflow process instance;
setting values of workflow relevant data associated with the workflow process instance based on the structured sentence attributes and structured sentence attribute values in the structured sentence for service; and
configuring the workflow process instance so that, once the workflow process instance is initiated, the system will execute the workflow process instance using information regarding tasks, routes, decision steps, tasks firing conditions and routing rules that are defined in the corresponding workflow process specification.

34. The apparatus for generating a service plan and associated electronic workflow for a customer comprising:
means for creating in an electronic storage area, the service plan for the customer, the service plan including a plurality of structured sentences for each of a plurality of specific customer needs of customers, said plurality of structured sentences including structured sentences for services, each structured sentence for service identifying a needed service corresponding to one of the specific customer needs, wherein the means for creating the service plan with structured sentences therein includes:
means for creating a structured sentence in the service plan for certain structured sentence data items, wherein the means for creating the structured sentence includes:
means for creating a structured sentence subject based on the subject in the corresponding structured sentence data item,
means for creating a structured sentence attribute based on an attribute in the corresponding structured sentence data item, and
means for setting a structured sentence attribute value based on a default attribute value specified in the corresponding attribute of the corresponding structured sentence data item;
means for creating the electronic workflow, the electronic workflow being in addition to the service plan, and capable of assisting completion of each needed service, the means for creating including means for using certain ones of said structured sentences for service to create a workflow process instance for each needed service, wherein at least certain ones of the workflow process instances include a plurality of tasks corresponding to steps for providing one of the services to the particular customer, which one service relates to the corresponding structured sentence for service;
means for changing the structured sentence attribute value for at least one attribute for at least one structured sentence in the service plan from the default attribute value to a selected attribute value, wherein the means for changing the structured sentence attribute value includes means for displaying a list of possible attribute values specified for the corresponding attribute of the structured sentence data item; and
means for selecting one of the possible attribute values from the displayed list as the selected attribute value.

35. An apparatus according to claim 34 wherein certain of the attributes associated with the structured sentences for services contain a selected attribute value chosen from among a group of possible attribute values.

36. An apparatus according to claim 35 wherein certain ones of said workflow process instances have at least one decision step, task firing condition or routing rule that create a plurality of possible sequences of tasks that are invoked as part of the execution of said workflow process instances.

37. An apparatus according to claim 36 further including means for modifying at least one of the structured sentence attributes, which modification also causes a change to the sequence of tasks invoked within at least one of the workflow process instances.

38. An apparatus according to claim 36 wherein selecting a different one of the possible attributes from among the group of possible attributes will result in the selection of a different one of the plurality of possible routes with respect to an associated decision step, task firing condition or routing rule.

39. An apparatus according to claim 34, wherein the service plan is a care plan, the customer is a patient, and the plurality of specific needs of the particular customer are health related problems of the particular customer.

40. An apparatus according to claim 39, wherein the means for creating the service plan includes means for transmitting a draft of the plurality of structured sentences among an interdisciplinary team of clinicians, said means for transmitting implementing a workflow automation process.

41. The apparatus according to claim 40 where the service plan, including the plurality of structured sentences, is created by the interdisciplinary team of clinicians using a workflow automation process to route a draft of the service plan, including the plurality of structured sentences therein, to the interdisciplinary team.

42. An apparatus according to claim 34 wherein the means for creating the electronic workflow includes means for creating an alert that will signify that an action needs to be taken.

43. An apparatus according to claim 34 further including means for automatically generating a translation of the service plan and means for transmitting the translation of the service plan to the customer.

44. An apparatus according to claim 43 further including means for revising the automatically generated translation.

45. An apparatus according to claim 43 wherein the means for transmitting transmits the translation to a remote computer associated with the customer.

46. An apparatus according to claim 34 further including means for creating other structured sentences, said other structured sentences including structured sentences for a goal, a fact, a protocol, and a finding.

47. An apparatus according to claim 34 further including means for initiating the associated electronic workflow.

48. An apparatus according to claim 47 further including means for updating status information for the service plan as the electronic workflow progresses.

49. An apparatus according to claim 48 wherein updates are provided to a user of the service plan in one form and updates are provided to the customer in another form.

50. An apparatus according to claim 49 wherein the one form is directed to a clinician and the other form is directed to a nonmedical person.

51. A method for generating a service plan that describes a plurality of services and associated workflow for a customer using a computer based system comprising the steps of: creating the service plan, the service plan including a plurality of structured sentences for each of a plurality of specific needs of a particular customer in an electronic storage area, wherein some of said plurality of structured sentences have a subject and an attribute contained therein, wherein certain of the attributes associated with the structured sentences for services contain a selected attribute value chosen from among a group of possible attribute values, and wherein the plurality of structured sentences together form a part of the service plan, said plurality of structured sentences including structured sentences for services, each structured sentence for service identifying a needed service corresponding to one of the specific customer needs, wherein the step of creating the service plan includes the steps of:

creating a structured sentence subject based on a subject in a corresponding structured sentence data item, creating a structured sentence attribute based on an attribute in the corresponding structured sentence data item, and setting a structured sentence attribute value based on a default attribute value specified in the corresponding attribute of the corresponding structured sentence data item;

creating the electronic workflow in addition to the service plan, which is adapted to assist in providing each needed service, the step of creating the electronic workflow including the step of using certain ones of said structured sentences for service to create a workflow process instance for each needed service, wherein at least certain ones of the workflow process instances include a plurality of tasks corresponding to steps for providing one of the services to the particular customer, which one service relates to the corresponding structured sentence for service;

changing the structured sentence attribute value for at least one attribute for at least one structured sentence in the service plan from the default attribute value to a selected attribute value, wherein the step of changing the structured sentence attribute value includes the step of displaying a list of possible attribute values specified for the corresponding attribute of the structured sentence data item; and selecting one of the possible attribute values from the displayed list as the selected attribute value.

52. A method according to claim 51 wherein the certain ones of said workflow process instances have at least one decision step, task firing condition or routing rule that creates a plurality of possible sequences of tasks, one sequence of which becomes the plurality of tasks invoked as part of a further step of executing one of said workflow process instances.

53. A method according to claim 52 further including the step of modifying at least one of the structured sentence attributes, which modification also causes a change to the one sequence of tasks invoked within the one workflow process instance.

54. A method according to claim 52 wherein selecting a different one of the possible attributes from among the group of possible attributes will result in the selection of a different one of the plurality of possible routes with respect to an associated decision step, task firing condition or routing rule.

55. A method according to claim 51 wherein the service plan is a care plan, the customer is a patient, and the plurality of specific customer needs are health related problems to be addressed as part of the patient's care.

56. A method according to claim 55, wherein the step of creating the plurality of structured sentences is created by an interdisciplinary team of clinicians.

57. The method according to claim 56 where the service plan, including the plurality of structured sentences, is created by the interdisciplinary team of clinicians using a workflow automation process to route a draft of the service plan, including the plurality of structured sentences therein, to the interdisciplinary team.

58. A method according to claim 51 wherein the step of creating the electronic workflow includes creating an alert that will signify that an action needs to be taken.

59. A method according to claim 51 further including the steps of automatically generating a translation of the service plan and transmitting the translation of the service plan to the customer.

60. A method according to claim 59 further including the step of revising the automatically generated translation prior to the step of transmitting.

61. A method according to claim 59 wherein the step of transmitting transmits the translation to a remote computer associated with the customer.

62. A method according to claim 51 further including the step of creating other structured sentences, said other structured sentences including structured sentences for a goal, a fact, a protocol, and a finding.

63. A method according to claim 51 further including the step of initiating the workflow.

64. A method according to claim 63 further including updating status information for the service plan as workflow progresses.

65. A method according to claim 64 wherein updates are provided to a user of the service plan in one form and updates are provided to the customer in another form.

66. A method according to claim 65 wherein the one form is directed to a clinician and the other form is directed to a nonmedical person.

67. A method according to claim 64 wherein the step of updating the status information for the service plan includes modifying an attribute contained in one of the structured sentences.

68. A method according to claim 64 wherein the step of updating the status information for the service plan includes adding another structured sentence relating to services.

69. The method according to claim 51 wherein the step of using each structured sentence for service to create the workflow process instance include the steps of:

matching the structured sentence to a corresponding workflow process specification;

creating a new workflow process instance;

setting values of workflow relevant data associated with the workflow process instance based on the structured sentence attributes and structured sentence attribute values in the structured sentence for service; and configuring the workflow process instance so that, once the workflow process instance is initiated, the system will execute the workflow process instance using information regarding tasks, routes, decision steps, tasks firing conditions and routing rules that are defined in the corresponding workflow process specification.

70. The method according to claim 51 wherein the plurality of structured sentences, including structured sentences for service, in service plan, are displayed together to the user with the appearance of a textual document.

71. The method according to claim 70 further including the step of creating other structured sentences, said other structured sentences including structured sentences for a goal, a fact, a protocol, and a finding.

* * * * *